US008461373B2

(12) United States Patent
Suzuki et al.

(10) Patent No.: US 8,461,373 B2
(45) Date of Patent: Jun. 11, 2013

(54) CATALYST FOR PRODUCING CARBOXYLIC ACID ESTERS, PROCESS FOR PRODUCING SAME AND PROCESS FOR PRODUCING CARBOXYLIC ACID ESTERS

(75) Inventors: Ken Suzuki, Tokyo (JP); Tatsuo Yamaguchi, Tokyo (JP)

(73) Assignee: Asahi Kasei Chemicals Corporation, Tokyo (JP)

(*) Notice: Subject to any disclaimer, the term of this patent is extended or adjusted under 35 U.S.C. 154(b) by 149 days.

(21) Appl. No.: 12/673,159

(22) PCT Filed: Jul. 31, 2008

(86) PCT No.: PCT/JP2008/063767
§ 371 (c)(1),
(2), (4) Date: Feb. 11, 2010

(87) PCT Pub. No.: WO2009/022544
PCT Pub. Date: Feb. 19, 2009

(65) Prior Publication Data
US 2011/0184206 A1    Jul. 28, 2011

(30) Foreign Application Priority Data

Aug. 13, 2007  (JP) ................. 2007-210962
Oct. 11, 2007  (JP) ................. 2007-265375
Oct. 26, 2007  (JP) ................. 2007-279411
Apr. 14, 2008  (JP) ................. 2008-105103

(51) Int. Cl.
| C07C 69/76 | (2006.01) |
| C07C 67/00 | (2006.01) |
| B01J 23/00 | (2006.01) |
| B01J 21/00 | (2006.01) |
| B01J 20/00 | (2006.01) |

(52) U.S. Cl.
USPC .......... 560/103; 560/208; 560/238; 502/238; 502/243; 502/252; 502/259; 502/261; 502/262; 502/263; 502/326; 502/330; 502/332; 502/333; 502/334; 502/335; 502/337; 502/339; 502/344; 502/347; 502/348; 502/355; 502/407; 502/415; 502/439

(58) Field of Classification Search
USPC ......... 502/259, 262–263, 302–304, 326–328, 502/330–335, 337, 339–341, 344–348, 355, 502/406, 407, 410, 411, 415, 439; 977/773, 977/775; 560/103, 208, 238
See application file for complete search history.

(56) References Cited

U.S. PATENT DOCUMENTS 3,901,827 A * 8/1975 Sinfelt et al. ............... 502/245
3,953,363 A * 4/1976 Yamauchi et al. .......... 502/178
(Continued)

FOREIGN PATENT DOCUMENTS
CN   1123527 A        5/1996
DE   10 2005 041 532 A1   3/2007
(Continued)

OTHER PUBLICATIONS

Fuson, R. C. et al., "Double Bond Migration in 1,2-Diaroyl-l-cycloalkenes," The Journal of Organic Chemistry, vol. 27, No. 5, pp. 1957-1961, (1962).
(Continued)

*Primary Examiner* — Cam N. Nguyen
(74) *Attorney, Agent, or Firm* — Finnegan, Henderson, Farabow, Garrett & Dunner, L.L.P.

(57) ABSTRACT

Disclosed is a catalyst for use in production of carboxylic acid ester by reacting (a) aldehyde and alcohol, or (b) one or more types of alcohols, in the presence of oxygen; wherein oxidized nickel and X (wherein X represents at least one element selected from the group consisting of nickel, palladium, platinum, ruthenium, gold, silver and copper) are loaded onto a support within the range of the atomic ratio of Ni/(Ni+X) of from 0.20 to 0.99.

18 Claims, 5 Drawing Sheets

U.S. PATENT DOCUMENTS

| | | | | |
|---|---|---|---|---|
| 4,035,263 A * | 7/1977 | Umemura et al. | | 502/242 |
| 4,374,046 A * | 2/1983 | Antos | | 502/327 |
| 4,518,796 A | 5/1985 | Aoshima et al. | | |
| 4,536,482 A * | 8/1985 | Carcia | | 502/5 |
| 4,562,174 A * | 12/1985 | Stiles | | 502/174 |
| 4,698,324 A * | 10/1987 | Haruta et al. | | 502/243 |
| 4,711,870 A * | 12/1987 | Yamada et al. | | 502/303 |
| 4,959,338 A * | 9/1990 | Miura et al. | | 502/263 |
| 4,992,408 A * | 2/1991 | Jackson | | 502/328 |
| 5,002,922 A * | 3/1991 | Irgang et al. | | 502/331 |
| 5,094,996 A * | 3/1992 | Kidd | | 502/405 |
| 5,254,705 A * | 10/1993 | Hattori et al. | | 554/141 |
| 5,347,046 A | 9/1994 | White et al. | | |
| 5,472,928 A * | 12/1995 | Scheuerman et al. | | 502/305 |
| 5,494,879 A * | 2/1996 | Jin et al. | | 502/314 |
| 5,506,273 A * | 4/1996 | Haruta et al. | | 518/713 |
| 5,883,036 A * | 3/1999 | Fujie et al. | | 502/217 |
| 6,057,442 A * | 5/2000 | Wulff-Doring et al. | | 544/106 |
| 6,228,800 B1 * | 5/2001 | Yamaguchi et al. | | 502/339 |
| 6,432,868 B1 * | 8/2002 | Marchal-George et al. | | 502/229 |
| 6,635,191 B2 * | 10/2003 | Figueroa et al. | | 252/373 |
| 6,660,897 B1 * | 12/2003 | Marchal-George et al. | | 585/482 |
| 6,706,659 B2 * | 3/2004 | Gillespie et al. | | 502/217 |
| 6,723,678 B2 * | 4/2004 | Gorer | | 502/326 |
| 6,846,471 B2 * | 1/2005 | Hotta et al. | | 423/239.1 |
| 6,861,387 B2 * | 3/2005 | Ruth et al. | | 502/184 |
| 6,921,605 B2 * | 7/2005 | Gorer | | 429/524 |
| 7,005,059 B1 * | 2/2006 | Quartararo et al. | | 208/213 |
| 7,005,405 B2 * | 2/2006 | Suenaga et al. | | 502/439 |
| 7,109,145 B2 * | 9/2006 | Ruth et al. | | 502/326 |
| 7,119,045 B2 * | 10/2006 | Magna et al. | | 502/313 |
| 7,268,097 B2 * | 9/2007 | Katsuno et al. | | 502/259 |
| 7,361,626 B2 * | 4/2008 | Baijense et al. | | 502/329 |
| 7,422,995 B2 * | 9/2008 | Baijense et al. | | 502/329 |
| 7,528,092 B2 * | 5/2009 | Berben et al. | | 502/251 |
| 7,662,740 B2 * | 2/2010 | Chondroudis et al. | | 502/180 |
| 7,811,965 B2 * | 10/2010 | Cendak et al. | | 502/326 |
| 2003/0060655 A1 | 3/2003 | Hayashi et al. | | |
| 2005/0131255 A1* | 6/2005 | Benderly et al. | | 562/546 |
| 2006/0084830 A1 | 4/2006 | Ryu | | |
| 2007/0179320 A1 | 8/2007 | Hirota et al. | | |
| 2007/0191651 A1 | 8/2007 | Coupard et al. | | |
| 2008/0177111 A1 | 7/2008 | van Laar et al. | | |
| 2008/0242537 A1 | 10/2008 | Kubanek et al. | | |

FOREIGN PATENT DOCUMENTS

| | | |
|---|---|---|
| DE | 10 2007 004 558 A1 | 8/2007 |
| EP | 1 358 935 B1 | 5/2003 |
| EP | 1 518 600 A1 | 3/2005 |
| FR | 2 882 531 A1 | 9/2006 |
| JP | 45-34368 | 11/1970 |
| JP | 55-153743 | 11/1980 |
| JP | 62-7902 | 2/1987 |
| JP | 7-313880 | 12/1995 |
| JP | 2000-154164 | 6/2000 |
| JP | 2001-220367 | 8/2001 |
| JP | 2002-361086 | 12/2002 |
| JP | 2003-53188 | 2/2003 |
| JP | 2003-103174 | 4/2003 |
| JP | 2006-212571 | 8/2006 |
| WO | WO 00/43121 | 7/2000 |
| WO | WO 2005/037768 A1 | 4/2005 |
| WO | WO 2007/015620 A1 | 2/2007 |

OTHER PUBLICATIONS

Choudary, B. M. et al., "The First Example of Activation of Molecular Oxygen by Nickel in Ni-Al Hydrotalcite: A Novel Protocol for the Selective Oxidation of Alcohols," Angewandte Chemie Int. Ed., vol. 40, No. 4, pp. 763-766, (2001).

Kawabata, T. et al., "Nickel Containing Mg-Al hydrotalcite-type anionic clay catalyst for the oxidation of alcohols with molecular oxygen," Journal of Molecular Catalysis A: Chemical 236, pp. 206-215, (2005).

Dai, Q. X. et al., "Photodegradation Catalyst Screening by Combinatorial Methodology," Applied Catalysis A: General 290, pp. 25-35, (2005).

Ferreira, F. F. et al., "Theoretical Optical Properties of Composite Metal-NiO Films," Journal of Physics D: Applied Physics, vol. 36, No. 19, pp. 2386-2392, (2003).

Kunio Nakagawa et al., "Oxidation with Nickel Peroxide. I. Oxidation of Alcohols," Organic Chemistry, vol. 27, No. 5, pp. 1597-1601, May 1962.

European Search Report for Corresponding EP Application No. 08791982.5-1270 dated Nov. 7, 2011.

International Preliminary Report on Patentability dated Mar. 18, 2010.

Barrio, V.L. et al., "Evaluation of Silica-Alumina-Supported Nickel Catalysts in Dibenzothiophene Hydrodesulphurisation," Applied Catalysis A: General 248 pp. 211-225 (2003).

Office Action for TW Application No. 097130712 mailed Jul. 30, 2012.

CN Office Action for Corresponding CN Application No. 200880102565.3 dated Mar. 1, 2012.

\* cited by examiner

| MEASUREMENT POINT | Ni/Au ATOMIC RATIO |
|---|---|
| 1 | 0.73 |
| 2 | 2.95 |
| 3 | DETECTION OF TRACE AMOUNT OF Ni ONLY |

(1)

(2)

CATALYST FOR PRODUCING CARBOXYLIC ACID ESTERS, PROCESS FOR PRODUCING SAME AND PROCESS FOR PRODUCING CARBOXYLIC ACID ESTERS

CROSS REFERENCE TO RELATED APPLICATIONS

This application is a national phase application based on PCT/JP2008/063767, filed Jul. 31, 2008, which claims the priority of Japanese Patent Application Nos. 2007-210962, filed Aug. 13, 2007; 2007-265375, filed Oct. 11, 2007; 2007-279411, filed Oct. 26, 2007; and 2008-105103, filed Apr. 14, 2008, the content of all of which is incorporated herein by reference.

TECHNICAL FIELD

The present invention relates to a catalyst for use in production of carboxylic acid esters by reacting an aldehyde and an alcohol, or one or more types of alcohols, in the presence of oxygen, to a process for producing the catalyst, and to a process for producing carboxylic acid esters using the catalyst.

BACKGROUND ART

A process for producing useful carboxylic acid esters industrially, in the case of methyl methacrylate, for example, may include a process in which methacrylic acid is produced by oxidizing methacrolein with oxygen followed by reacting the methacrylic acid with methanol to product methyl methacrylate. However, the heteropolyacid catalyst used in a step for obtaining methacrylic acid by oxidizing methacrolein has problems with thermal stability, and gradually decomposes under reaction temperature conditions. In addition, the yield is also still not adequate, thus leaving room for improvement as an industrial catalyst.

On the other hand, the direct metha process for producing methyl methacrylate or methyl acrylate in a single step by reacting methacrolein or acrolein with methanol and molecular oxygen is a simple process that does not require separation of easily polymerizable methacrylic acid or acrylic acid, and is currently attracting attention because of its higher yield of methyl methacrylate in comparison with the above process.

In such a process, a catalyst primarily containing palladium is used for the catalyst. However, during production of methyl methacrylate or methyl acrylate in a single step by reacting methacrolein or acrolein with methanol and molecular oxygen, since the methacrolein or acrolein is an unsaturated aldehyde, numerous acetals of the unsaturated aldehyde and alkoxy forms, resulting from addition of alcohol to the unsaturated bonds, are formed as by-products, while also resulting in the problem of generation of carbon dioxide gas which is the final oxidation product (see Patent document 1).

Therefore, modifications have been made to the catalyst to overcome these problems. For example, the above problems regarding the formation of the by-products have been reported to be solved and carboxylic acid ester has been reported to be able to be produced at high yield by using a catalyst containing an intermetallic compound containing palladium and at least one element selected from the group consisting of lead, mercury, bismuth and thallium, or a catalyst containing an alkaline metal compound or alkaline earth metal compound (see Patent Document 2).

On the other hand, although the presence of a catalyst containing palladium was long thought to be required for catalysts used in this process, more recently, catalysts have been reported to have been used that comprise the loading of a noble metal such as ruthenium or gold on a support. Specific examples of such processes include the use of a catalyst in which gold is loaded onto a support (see Patent document 3) or the use of a catalyst comprised of ruthenium (see Patent document 4) during production of carboxylic acid ester by reacting aldehyde and alcohol in the presence of an oxygen-containing gas.

Patent document 1: Japanese Patent Publication No. S45-34368
Patent document 2: Japanese Patent Publication No. S62-7902
Patent document 3: Japanese Patent Application Laid-open No. 2000-154164
Patent document 4: Japanese Patent Application Laid-open No. 2001-220367

DISCLOSURE OF INVENTION

Problems to be Solved by the Invention

However, in each of the known processes described above, the selectivity of the resulting carboxylic acid esters and catalyst activity are inadequate, and since expensive noble metals such as palladium, ruthenium and gold are used by loading onto a support in high amounts, the economic burden resulting from increased catalyst production costs is large, thus making it difficult to consider these processes to be industrially advantageous processes.

In addition, since the palladium, ruthenium and gold which are used in the above production processes are types of noble metals, they are expensive, and when as a catalyst component, they are frequently used by dispersing and loading onto a support, thus making the selection of a support extremely important in such cases.

On an assumption of putting industrial process into a practical use, as a result of conducting extensive studies on catalysts loaded with composite nanoparticles containing oxidized nickel and X (wherein X represents at least one element selected from the group consisting of nickel, palladium, platinum, ruthenium, gold, silver and copper), the inventors of the present invention clearly concluded that a satisfactory catalyst from the viewpoint of catalyst life was not necessarily obtained in the case of using activated carbon, calcium carbonate, alumina, silica or silica-titania as the support. Namely, in the case of reacting a catalyst in the form of a slurry in a commonly used industrial stirring tank reactor or bubble tower reactor and the like, mechanical strength was inadequate and exfoliation of nickel and component X which are the catalyst components was observed in the case of activated carbon. In addition, although alumina has high mechanical strength, the strength of the support decreases due to corrosion by acidic substances exemplified by characteristic by-products of the reaction, methacrylic acid and acrylic acid, thereby resulting in the shortcoming of greater ease of exfoliation of nickel and component X which are the catalyst components. The use of calcium carbonate for the support results in even greater susceptibility to the occurrence of corrosion by acidic substances than in the case of alumina, thereby making it unsuitable for industrial use. In the case of silica or silica-titania, a portion of the silica is gradually eroded by water introduced along with the process or by water produced as a by-product of the reaction, thereby resulting in the phenomenon of the elution of silica, while exfoliation and elution of nickel and component X which are catalyst components are also simultaneously observed. Consequently, there are problems as to whether these substances will remain stable over the course of long-term use. In addition, there are also the problems of mechanical strength being lower than the above-mentioned alumina.

On the other hand, studies on processes for producing silica gel and studies on the use of high-temperature sintering to modify silica gel have been reported for the purpose of improving the mechanical strength and corrosion resistance of silica. However, there have been no examples reported of successfully improving mechanical strength and hydrolysis stability without impairing the inherent performance of the catalyst. For example, quartz, which is a type of silica-based substance, is known to be hard, have high mechanical strength and have high hydrolysis resistance. However, in the case of using quartz as a support, although mechanical strength and corrosion resistance are remarkably improved, this also leads to a decreased in specific surface area (1 $m^2/g$ or less), and since this prevents metal catalyst from being loaded in the form of fine particles in a highly dispersed state, the problem results in the extremely low reactivity of the resulting catalyst.

On the basis of this background as described above, there is currently a need for a catalyst support that has high mechanical strength and is physically stable while also having a high surface area suitable for use as a catalyst support, demonstrates satisfactory corrosion resistance with respect to the characteristic liquid nature of the reaction in the form of a carboxylic acid ester synthesis reaction in the presence of oxygen, and is capable of stably loading nickel and component X which are catalyst active components over a long period of time.

With the foregoing in view, an object of the present invention is to provide a catalyst for use in production of carboxylic acid ester by reacting aldehyde and alcohol, or one or more types of alcohols, in the presence of oxygen, wherein a high level of reactivity is maintained by using as main catalyst components stable metal elements having superior reactivity instead of conventional expensive noble metals, to provide a process for producing the catalyst, and to provide a process for producing carboxylic acid esters using the catalyst.

Means for Solving the Problems

As a result of conducting extensive studies to solve the above-mentioned problems, the inventors of the present invention found that the above problems can be solved by a catalyst for producing carboxylic acid ester in which oxidized nickel and X (wherein, X represents at least one element selected from the group consisting of nickel, palladium, platinum, ruthenium, gold, silver and copper) are loaded onto a support within the range of an atomic ratio of Ni/(Ni+X) of from 0.20 to 0.99.

Namely, the present invention is as described below.

[1] A catalyst for use in production of carboxylic acid ester by reacting (a) aldehyde and alcohol, or (b) one or more types of alcohols, in the presence of oxygen, comprising:
oxidized nickel; and
X (wherein X represents at least one element selected from the group consisting of nickel, palladium, platinum, ruthenium, gold, silver and copper) loaded onto a support within a range of an atomic ratio of Ni/(Ni+X) of from 0.20 to 0.99.

[2] The catalyst for use in production of the carboxylic acid ester according to item [1], comprising a composite nanoparticle composed of the oxidized nickel and the X (wherein X represents at least one element selected from the group consisting of nickel, palladium, platinum, ruthenium, gold, silver and copper).

[3] The catalyst for use in production of the carboxylic acid ester according to item [2], wherein the composite nanoparticle is a particle having X at a core thereof and a surface of the core is covered with the oxidized nickel.

[4] The catalyst for use in production of the carboxylic acid ester according to item [2] or [3], wherein the oxidized nickel is further independently loaded onto the support, in addition to the composite nanoparticle.

[5] The catalyst for use in production of the carboxylic acid ester according to any of items [1] to [4], wherein the oxidized nickel is a nickel oxide and/or a composite oxide containing nickel.

[6] The catalyst for use in production of the carboxylic acid ester according to any of items [1] to [5], wherein the support is an aluminum-containing silica-based composition containing silica and alumina, and an amount of aluminum is within a range of from 1 to 30 mol %, based on a total molar amount of the silicon and the aluminum.

[7] The catalyst for use in production of the carboxylic acid ester according to item [6], wherein the support further comprises at least one species of basic metal component selected from the group consisting of an alkaline metal, an alkaline earth metal and a rare earth metal.

[8] The catalyst for use in production of the carboxylic acid ester according to item [6] or [7], wherein a compositional ratio of nickel to alumina is from 0.01 to 1.0 in terms of an atomic ratio of Ni/Al.

[9] The catalyst for use in production of the carboxylic acid ester according to item [7] or [8], wherein a compositional ratio of nickel to the basic metal component is from 0.01 to 1.2 in terms of an atomic ratio of Ni/(the alkaline metal+the alkaline earth metal+the rare earth metal).

[10] The catalyst for use in production of the carboxylic acid ester according to any one of items [1] to [9], wherein the support is a silica-alumina-magnesia composition containing silica, alumina and magnesia, and comprises silicon at 42 to 90 mol %, aluminum at 5.5 to 38 mol % and magnesium at 4 to 38 mol %, based on a total molar amount of silicon, aluminum and magnesium.

[11] The catalyst for use in production of the carboxylic acid ester according to item [10], wherein the composition ratio of nickel to alumina is from 0.01 to 1.0 in terms of the atomic ratio of Ni/Al, and the composition ratio of nickel to magnesia is from 0.01 to 1.2 in terms of an atomic ratio of Ni/Mg.

[12] The catalyst for use in production of the carboxylic acid ester according to any of items [1] to [11], wherein a specific surface area is from 20 to 350 $m^2/g$, a maximum frequency of a pore diameter is from 3 to 50 nm, a pore volume is from 0.1 to 1.0 mL/g, and a particle diameter is from 10 to 200 μm.

[13] A process of producing a catalyst for use in production of carboxylic acid ester, comprising:
a first step of obtaining a catalyst precursor by precipitating nickel and a component X (wherein X represents at least one element selected from the group consisting of nickel, palladium, platinum, ruthenium, gold, silver and copper) on a support by neutralizing an acidic solution of a soluble metal salt containing nickel and X; and
a second step of oxidizing the nickel by heat-treating the obtained catalyst precursor.

[14] A process for producing carboxylic acid ester comprising a step of reacting the catalyst for use in production of carboxylic acid ester according to any one of items [1] to [12], with (a) aldehyde and alcohol, or (b) one or more types of alcohols, in the presence of oxygen.

[15] The process for producing carboxylic acid ester according to item [14], wherein the aldehyde is a compound selected from acrolein, methacrolein and a mixture thereof.

[16] The process for producing carboxylic acid ester according to item [14], wherein the aldehyde is a compound selected from acrolein, methacrolein and a mixture thereof, and the alcohol is methanol.

[17] The process for producing carboxylic acid ester according to item [14], wherein one type of the alcohol is ethylene glycol, and another type of the alcohol is methanol.

Advantageous Effects of the Invention

According to the present invention, a catalyst for use in production of carboxylic acid ester, which maintains a high level of reactivity by using for the main catalyst component a stable nickel compound having superior reactivity instead of the conventional expensive noble metals, a process for producing the catalyst, and a process for producing carboxylic acid ester using the catalyst, can be provided.

BEST MODE FOR CARRYING OUT THE INVENTION

Figure 1:
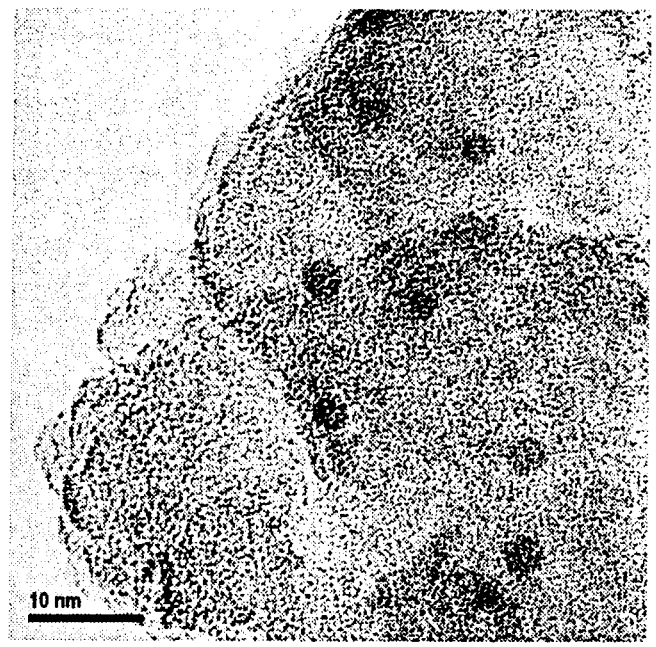
FIG. 1 shows a photomicrograph obtained with a transmission electron microscope (TEM bright field image) of a catalyst for use in production of carboxylic acid ester of Example 4.

The following provides a detailed explanation of the best mode for carrying out the present invention (referred to as "the present embodiment"). Furthermore, the present invention is not limited to the following embodiments, but rather can be carried out by altering in various ways within the scope of the present invention.

The catalyst for use in production of carboxylic acid ester according to the present embodiment is a catalyst for use in production of carboxylic acid ester by reacting (a) aldehyde and alcohol, or (b) one or more types of alcohols, in the presence of oxygen, wherein oxidized nickel and X (wherein X represents at least one element selected from the group consisting of nickel, palladium, platinum, ruthenium, gold, silver and copper) are loaded onto a support within a range of an atomic ratio of Ni/(Ni+X) of from 0.20 to 0.99.

The catalyst for use in production of carboxylic acid ester according to the present embodiment preferably further comprises composite nanoparticles composed of oxidized nickel and X (wherein X represents at least one element selected from the group consisting of nickel, palladium, platinum, ruthenium, gold, silver and copper).

The oxidized nickel is preferably a nickel oxide formed by bonding nickel and oxygen (such as $Ni_2O$, $NiO$, $NiO_2$, $Ni_3O_4$ or $Ni_2O_3$), or a composite oxide containing nickel, such as a nickel oxide compound, solid solution or mixture thereof, formed by bonding nickel and X and/or one or more types of another metal element and oxygen.

The term "nickel oxide" used herein refers to a compound containing nickel and oxygen. The nickel oxide includes $Ni_2O$, $NiO$, $NiO_2$, $Ni_3O_4$ or $Ni_2O_3$, or hydrates of the foregoing, hydroperoxides of nickel containing a OOH group or peroxides of nickel containing a $O_2$ group, or a mixture of the foregoing, and the like.

In addition, the term "composite oxide" used herein refers to an oxide containing two or more types of metals. The term "composite oxide" refers to an oxide in which two or more types of metal oxides form a compound, and although this includes double oxides in which ions of oxoacids are not present as structural units (such as perovskite-oxides or spinel-type oxides of nickel), it also includes all oxides in a broader sense than double oxides in which two or more types of metals are compounded. Oxides in which two or more types of metal oxides form a solid solution also fall within the scope of compound oxides.

The following provides an explanation of the action by which extremely high catalyst performance is demonstrated by loading oxidized nickel and X (wherein X represents at least one element selected from the group consisting of nickel, palladium, platinum, ruthenium, gold, silver and copper) onto a support within a range of an atomic ratio of Ni/(Ni+X) of from 0.20 to 0.99.

The inventors of the present invention found that the inherent catalyst activity of nickel oxides having oxidative esterification activity is achieved by compounding the nickel oxide and X, and that remarkably high catalyst performance is demonstrated that is not demonstrated with catalysts composed of each individual component. This is attributable to a unique effect demonstrated as a result of compounding the nickel oxide and X, and is thought to be the result of the creation of a novel catalytic action that is completely different from that of catalysts consisting of each individual component due to, for example, the formation of a binary functional catalyst or a novel active species between both metal components. On the basis of this novel concept, in the case of loading the oxidized nickel and X onto the support in a highly dispersed state, revolutionary catalyst performance in particular was able to be realized unlike that obtained with catalysts of the prior art.

In recent years, nanoparticles, which have attracted considerable attention due to advances made in ultrafine particle synthesis technology, are recognized to be a basic material in the field of nanotechnology, and research thereon is progressing around the world. Nanoparticles having a particle diameter of 100 nm or less differ from bulk particles in that they have a high proportion of surface metal element among the metal elements that constitute the nanoparticles, thus resulting in the surface area of the metal element per unit mass increasing rapidly the smaller the particle size. Examples of nanoparticles known in the field of catalyst materials may include metal nanoparticles such as those of platinum, palladium, ruthenium, rhodium, gold, silver and copper, or metal oxide nanoparticles such as those of iron oxide, cobalt oxide, nickel oxide, zinc oxide, titanium oxide, zirconium oxide, indium oxide, alumina and silica, and these nanoparticles are attracting attention as heterogeneous catalyst materials. Namely, one reason for the growing attention being placed on the application of nanoparticles to catalyst materials is that, since that which contributes to the catalytic action is limited to the metal element present on the surface thereof, when applied on the nano level, the surface area per unit mass of the metal element involved in a reaction (specific surface area) increases, thereby improving the catalyst activity per metal element mass. Changes in catalytic action attributable to the particle size of nanoparticles in this manner are widely known in the form of "particle size effects".

On the other hand, there are also cases in which new effects are demonstrated in addition to these particle size effects. For example, the action of binary metal nanoparticles are known to be one of the factors having a significant effect on the catalytic action of nanoparticles. This action refers to an effect that is unable to be demonstrated by single metal species, and is only demonstrated as a result of compounding. Alloys as referred to in the prior art are a known example of this (binary metal nanoparticles refer not only to the case of the element species being a metal, but also includes cases in which metal compounds or metals and metal compounds are combined). Although particle size and shape are mainly the parameters to be controlled in the case of nanoparticles consisting of a single element, in the case nanoparticles are composed of two or more types of element species, additional control parameters include composition, crystal structure and phase structure (such as the alloy or solid solution structure in which crystal sites are randomly occupied by chemical species, core-shell structure in which each chemical species is separated in the form of concentric spheres, anisotropic phase structure in which phases are separated anisotropically, and heterobondphilic structure, in which both chemical species are present adjacent to each other on the surface of particles). Namely, as a result of employing a binary compound structure, changes in mass of the metal species occur resulting in the demonstration of chemical and electronic properties that are clearly different from single nanoparticles. Thus, binary metal nanoparticles were found to demonstrate novel catalytic, magnetic and optical properties not found in nanoparticles composed of single metal element species, and their applications are being developed in various fields such as electronic materials, medicine and biotechnology in addition to catalysts.

The inventors of the present conducted a wide-ranging search for materials for the purpose of developing catalysts having high carboxylic acid ester selectivity and activity while also having for the main component thereof an inexpensive metal element having superior reactivity to take the place of expensive noble metals of the prior art. Attention was focused on nickel as an element having properties that resemble those of noble metals, and extensive research was conducted on the correlation between chemical state and reactivity thereof, thereby leading to completion of the present invention. Namely, as was previously described, the catalyst of the present embodiment has oxidized nickel and X as a binary metallochemical species (wherein X represents at least one element selected from the group consisting of nickel, palladium, platinum, ruthenium, gold, silver and copper) loaded onto a support within a range of an atomic ratio of from Ni/(Ni+X) of 0.20 to 0.99. The catalyst of the present embodiment preferably further comprises nanoparticles composed of the oxidized nickel and X (wherein X represents at least one element selected from the group consisting of nickel, palladium, platinum, ruthenium, gold, silver and copper). The following provides a more detailed explanation thereof.

When the inventors of the present invention used nickel oxides, currently attracting attention as an alcohol oxidation catalyst, as a catalyst, it was found for the first time that despite a low level of activity, even nickel oxide (NiO) alone demonstrated carboxylic acid ester formation activity. Moreover, as a result of conducting additional research, the inventors of the present invention clearly demonstrated that highly oxidized nickel peroxide ($NiO_2$) demonstrates higher performance than that of nickel oxide. On the other hand, activity was not observed in the case of using nickel metal (Ni) alone.

On the basis of these findings, the possibility was suggested that an inexpensive metal element, nickel, can be used as the main component of a catalyst. Next, the inventors of the present invention examined the addition of various metal elements to nickel oxide by changing the oxidized state of nickel based on the approach of further increasing catalyst performance by controlling the oxidized state of nickel and loading an active component onto a support in a highly dispersed state. As a result, the inventors of the present invention found that by loading oxidized nickel and at least one metal component selected from the group consisting of nickel, palladium, platinum, ruthenium, gold, silver and copper onto a support in a highly dispersed state within a range of an atomic ratio of Ni/(Ni+X) of from 0.20 to 0.99, the nickel oxide is converted from a normal oxidized state to a highly oxidized nickel oxide, thereby dramatically improving activity and selectivity as compared with catalysts composed of each element alone or catalysts in which the atomic ratio of Ni/(Ni+X) is outside the above range.

For example, when gold is selected for X and nickel oxide and gold are loaded onto a support in a highly dispersed state, remarkably high catalyst activity is demonstrated. This catalyst was observed to demonstrate higher carboxylic acid ester selectivity as compared with catalysts in which nickel oxide or gold is loaded onto a support alone, and a considerable improvement in activity was observed for a specific composition ratio of Ni/(Ni+Au). With respect to the catalyst activity per metal atom, the carboxylic acid ester formation activity of (Ni+Au) demonstrates higher activity than catalysts composed of each component alone, and catalyst function attributable to compounding thereof is greatly dependent on the loaded composition of the nickel and gold. This is presumed to be due to being present at a ratio optimum for formation of a nickel oxidized state optimal for the reaction. In this manner, as a result of the two components of nickel oxide and gold being loaded while dispersed on a support, remarkable compounding effects were demonstrated that were unable to be predicted from simply adding the effects produced by each component alone.

In the above catalyst, oxidized nickel and gold are loaded onto a support in a highly dispersed state, and both components are compounded at the nano level. Based on the results of observations with a transmission electron microscope/scanning transmission electron microscope (TEM/STEM), nearly spherical nanoparticles having a particle diameter distribution of from 2 to 3 nm were loaded uniformly dispersed on the support. Based on an elementary analysis of the nanoparticles by energy dispersed X-ray spectroscopy (EDS), both nickel and gold are present in all of the particles, and were observed to be in the form of nickel coated on the surface of gold nanoparticles. In addition, nickel component alone was observed to be loaded on the support in addition to the nanoparticles containing nickel and gold.

According to the results of X-ray photoelectron spectroscopy (XPS) and powder X-ray diffraction (powder XRD), although the gold is present in the form of crystalline metal, the nickel is presumed to be present in the form of an amorphous oxide having a valence of 2.

On the basis of ultraviolet-visible spectroscopy (UV-Vis) capable of observing changes in electron excitation states, compound of the oxidized nickel oxide and gold was determined to cause disappearance of a surface plasmon absorption peak (at about 530 nm) originating from gold nanoparticles observed in gold nanoparticles composed of a single gold species. The disappearance of this surface plasmon absorption peak was not observed in combinations of gold and metal oxide species other than nickel oxide, for instance, chromium oxide, manganese oxide, iron oxide, cobalt oxide, copper oxide or zinc oxide, which combinations are observed to have no effect on the reaction. The disappearance of this surface plasmon absorption peak is thought to be the result of mixing electron states through the contact interface between the oxidized nickel and gold, or in other words, due to hybridization of two types of metallochemical species.

Conversion to highly oxidized nickel oxide can be observed by a color change in the catalyst and ultraviolet-visible spectroscopy (UV-Vis). As a result of adding gold to nickel oxide, the nickel oxide changed from grayish-green to brown, and the UV spectrum demonstrated absorbance throughout nearly the entire visible range. The shape and color of the UV spectrum resembled that of highly oxidized nickel peroxide ($NiO_2$) measured as a reference sample. On the basis of this finding, nickel oxide is presumed to be converted to highly oxidized nickel oxide by addition of gold.

On the basis of these results, the structure of composite nanoparticles is thought to be such that gold nanoparticles are located at the core and the surface of the gold nanoparticles is covered with highly oxidized nickel oxide, and gold atoms are not present on the surface of the composite nanoparticles.

[Presumed Principle of Action]

Next, an explanation is provided of the presumed principle of the action of the catalysts according to the present embodiment by using the example of modification and improvement of nickel compounds on which research has been conducted for use as catalysts and electronic materials.

Examples of the application of heterogeneous nickel compounds to oxidation reactions of the prior art may include (1) an alcohol oxidation process using nickel peroxide ($NiO_2$) as a stoichiometric oxidizing agent (J. Org. Chem. 27 (1962) 1597), (2) an oxygen-based alcohol oxidation reaction using Ni—Al hydrotalcite as a catalyst (Angew. Chem. Int. Ed. 40 (2001) 763), (3) an oxygen-based alcohol oxidation reaction using Mg—Al hydrotalcite containing Ni(II) as a catalyst (J. Mol. Catal. A 236 (2005) 206), (4) an oxygen-based alcohol oxidation reaction using nanoparticles of nickel peroxide ($NiO_2$) as a catalyst (Appl. Catal. A 290 (2005) 25) and the like.

Although highly oxidized nickel peroxide has a higher oxidation power than ordinary nickel oxide, and has long been known to be able to oxidize various alcohols stoichiometrically, as a result of the various modifications and improvements to nickel catalysts in recent years, catalytic oxidation reactions of alcohol with molecular oxygen have been realized. Nickel-hydrotalcite-based catalysts enable nickel to function as an oxygen activation sites by compounding nickel and dissimilar metal element (such as Al or Mg), and is thought to result in the formation of peroxo species serving as a reactive species on the nickel. In addition, in processes using nanoparticles of nickel peroxide, reactions have been reported to proceed catalytically as a result of forming the nickel peroxide into nanoparticles.

Nickel oxide is used as an electrochromic material, for example, in the field of electronic materials other than catalysts. In order to enhance the photoabsorption response rate of nickel oxide films, research has been conducted on (5) a compound film of NiO-Me (wherein, Me represents Au, Ag, Cu, Ni, Pd or Pt) in which metal (Me) is doped with nickel oxide (J. Phys. D: Appl. Phys. 36 (2003) 2386). Metals doped with nickel oxide act as holes, and the oxidation coloring rate is thought to be improved when nickel oxide is converted to a highly oxidized nickel oxide.

Such application examples of nickel compounds give important suggestions in terms of understanding the expression of catalyst function demonstrated by the catalyst of the present embodiment. Although the inventors of the present invention found that nickel peroxide demonstrates activity in carboxylic acid ester synthesis reactions, the level of the catalyst activity was low. Pure nickel peroxide and anhydrides thereof have yet to be obtained, there are many aspects of its structure that remain unclear, and it is also considered to be a form of nickel oxide (divalent) that has adsorbed oxygen. However, since nickel peroxide is extremely useful as a stoichiometric oxidizing agent, if it were possible to generate a catalytically active oxidizing active species by using molecular oxygen for the oxidizing agent, nickel peroxide could be applied to oxidation of organic substrates with molecular oxygen. Pioneering research in this field is described in (2) above, with this research resulting in achieving for the first time in the world oxygen oxidation by heterogeneous nickel catalyst as a result of realizing highly efficient activation of molecular oxygen by compounding nickel and a dissimilar metal element. In addition, as described in (4) above, a report indicating that nickel peroxide functions as a catalyst by converting to nanoparticles indicates the importance of control of geometrical structure in terms of expressing a catalyst active species.

In addition, examples of a method for controlling the oxidized state of nickel oxide used as an electrochromic material may include the combining of a group 8 metal and a group 1B metal as indicated in (5) above, thereby improving the conversion rate to highly oxidized nickel oxide. This suggests that in catalytic reactions as well, controlling the electronic state of oxidized nickel is possible by compounding with a specific metal, and this applies to the basic concept of the catalyst of the present embodiment as well.

As has been previously described, the structure of the composite nanoparticles of the present embodiment is presumed to comprises X particles serving as the core with highly oxidized nickel oxide covering the surface thereof. Based on (1) to (5) above, in the composite nanoparticles of the present embodiment, since the oxidized nickel and X interact at the atomic level, the electronic state of the nickel oxide is converted to a highly oxidized state, and changes in the geometrical structure of active sites thereof as well as changes in electronic properties can be considered to be reflected in its catalytic action. In addition, it is predicted that a novel active species mediated by oxygen atoms is formed at the contact interface between the nickel oxide and X, and this is thought to result in the creation of a novel catalyst function completely different from that in the case of using either component alone.

Namely, the catalyst for use in production of carboxylic acid ester according to the present embodiment is clearly different from conventional metal catalysts composed of a single metal species, binary metal catalysts such as alloys or intermetallic compounds, and binary catalysts composed of combinations of metal oxides other than nickel and metal elements, and the state change in active sites specifically expressed due to compounding of oxidized nickel and X are presumed to result in revolutionary catalyst performance unable to be obtained with catalysts of the prior art.

[Details of Catalyst for Use in Production of Carboxylic Acid Ester]

The catalyst for use in production of carboxylic acid ester according to the present embodiment is a catalyst in which oxidized nickel and X (wherein X represents at least one element selected from the group consisting of nickel, palladium, platinum, ruthenium, gold, silver and copper) are loaded onto a support within a range of an atomic ratio of Ni/(Ni+X) of from 0.20 to 0.99.

The catalyst according to the present embodiment preferably further comprises composite nanoparticles composed of oxidized nickel and X (wherein X represents at least one element selected from the group consisting of nickel, palladium, platinum, ruthenium, gold, silver and copper).

The oxidized nickel and X are preferably loaded onto the support in a highly dispersed state. The oxidized nickel and X are more preferably loaded while dispersed in the form of fine particles or a thin film, and the average particle diameter of each is preferably from 2 to 15 nm, more preferably from 2 to 10 nm, and even more preferably from 2 to 6 nm. Herein, the average particle diameter as referred to in the present embodiment refers to the number average particle diameter as measured with a transmission electron microscope (TEM).

The loaded composition of the nickel and X is such that the atomic ratio of Ni/(Ni+X) is within a range of from 0.20 to 0.99, preferably within a range of from 0.30 to 0.90 and more preferably within a range of from 0.50 to 0.90. The atomic ratio of Ni/(Ni+X) as referred to herein is the ratio of the number of nickel atoms loaded onto the support to the total number of nickel and X atoms. If the atomic ratio of Ni/(Ni+X) is within the above ranges, a specific active species structure composed of nickel and X and a nickel oxidized state suitable for the reaction are formed, and as a result thereof, activity and selectivity tend to be higher than catalysts in which the atomic ratio is outside these ranges.

In the case composite nanoparticles composed of oxidized nickel and X are contained in a catalyst, that catalyst is not limited to that in which nanoparticles are only loaded onto a support, but rather catalysts are also included in which oxidized nickel alone is loaded onto the support in addition to the composite nanoparticles.

The composite nanoparticle refers to a nanoparticle containing oxidized nickel and X (wherein X represents at least one element selected from the group consisting of nickel, palladium, platinum, ruthenium, gold, silver and copper).

Although there are no particular limitations on the form of the composite nanoparticles provided both components are contained therein, preferably both components are present in the nanoparticles, and the form preferably adopts a phase structure such as a solid solution structure in which crystal sites are randomly occupied by chemical species, a core-shell structure in which each chemical species is separated in the form of concentric spheres, an anisotropic phase structure in which phases are separated anisotropically, and a heterobondphilic structure, in which both chemical species are present adjacent to each other on the surface of particles. More preferably, X serves as a core, and oxidized nickel is coated on the surface thereof. There are no particular limitations on the shape of the composite nanoparticles provided both components are contained therein, and may have any shape such as spheres or hemispheres.

The composition of nickel and X in the composite nanoparticles is such that the atomic ratio of Ni/X is preferably within a range of from 0.1 to 10, more preferably within a range of from 0.2 to 5.0 and even more preferably within a range of from 0.3 to 3.0.

The range of the average particle diameter of the composite nanoparticles is preferably from 2 to 15 nm, more preferably from 2 to 10 nm and even more preferably from 2 to 6 nm.

In the case the composite nanoparticles are in the form of having X at the core and having oxidized nickel covering the surface thereof, the average particle diameter of X is preferably within a range of from 1.5 to 12 nm, more preferably within a range of from 2 to 10 nm and even more preferably within a range of from 2 to 6 nm in consideration of the balance between expression of activity and stability. The thickness of the surface nickel layer consisting of one or more layers of oxidized nickel molecules, and changes according to such factors as the loaded composition of nickel and X, the atomic ratio and particle diameter of nickel and X in the composite nanoparticles, and the manner in which the catalyst is prepared. The thickness of the nickel layer in terms of oxidized nickel molecules is preferably about from 1 to 5 layers, and more preferably about from 1 to 3 layers. In addition, a composite oxide may be formed within the composite nanoparticles that have emically bonded species such as Ni—O—X at the interface where both nickel and X components are in contact.

The reason for there being preferable ranges for the loaded composition of nickel and X and the atomic ratio of nickel and X in the composite nanoparticles, and the reason for allowing a margin, are that the proportion of surface atoms differs according to the particle diameter of X. For example, in citing the example of gold, at a gold particle diameter of 10 nm, the total number of atoms formed becomes about $2.1 \times 10^4$, and the proportion of the number of surface atoms becomes about 15%. If the particle diameter is 2 nm, the total number of atoms formed becomes about 150, and the proportion of the number of surface atoms becomes 63%. Thus, in the case of considering a form in which the surface of X is covered with nickel, it can be easily surmised that the atomic ratio of nickel and X differs depending on the particle diameter of X.

As previously described, a transmission electron microscope/scanning transmission electron microscope (TEM/STEM) is an effective analytical method for observing the morphology of the composite nanoparticles, and irradiating images of nanoparticles observed by TEM/STEM with an electron beam makes it possible to analyze elements within the nanoparticles and extract an image of the distribution of those elements. As will be indicated in the examples to be described later, the composite nanoparticles according to the present embodiment were confirmed to have a form in which nickel and X are contained in all of the particles and the surface of X is covered with nickel. In the case of adopting such a form, the atomic ratio of nickel and X differs according to the location of the composition analysis site in the nanoparticles, and larger amounts of nickel are detected on the edge of the particles than at the center of the particles. Thus, a margin is allotted for the atomic ratio of nickel and X depending on the location of the analysis site even for individual nanoparticles, and the range of that margin is included in the ranges of the atomic ratio of Ni/X as previously described.

In the case of having selected gold, silver or copper for X, ultraviolet-visible spectroscopy (UV-Vis) is an effective means of identifying the structure thereof. In the case of nanoparticles containing gold, silver or copper only, the photoelectric field of the visible-near infrared band couples with the surface free electrons of the metal resulting in surface plasmon absorption. For example, when a catalyst loaded with gold nanoparticles is irradiated with visible light, an absorption spectrum is observed based on plasmon resonance originating from the gold nanoparticles at a wavelength of about 530 nm. However, in the case of a catalyst loaded with nickel oxide and gold according to the present embodiment, the surface plasmon absorption thereof disappears, thereby suggesting the absence of gold on the surface of the catalyst according to the present embodiment.

Preferable examples of the oxidized nickel may include nickel oxides formed by bonding nickel and oxygen (such as $Ni_2O$, $NiO$, $NiO_2$, $Ni_3O_4$ or $Ni_2O_3$), and composite oxides containing nickel, such as a nickel oxide compounds, solid solutions or mixture thereof, formed by bonding nickel and X and/or one or more types of other metal elements and oxygen.

There are no particular limitations on the solid form of nickel provided it allows the obtaining of the prescribed catalyst activity, and is preferably in an amorphous state in which diffraction peaks are not observed by X-ray diffraction. As a result of employing such a form, since interaction with oxygen is presumed to be greater and the bonding interface between the oxidized nickel and X increases, even better catalyst activity tends to be obtained.

X represents at least one element selected from the group consisting of nickel, palladium, platinum, ruthenium, gold, silver and copper, and represents more preferably selected from the group consisting of nickel, palladium, ruthenium, gold and silver.

Although the chemical state of X may be a metal, oxide, hydroxide, composite compound containing X and nickel or one or more types of other metal elements, or any mixture thereof, the preferable chemical state is a metal or oxide, and more preferably a metal. In addition, there are no particular limitations on the solid form of X provided it allows the obtaining of the prescribed catalyst activity, and may be crystalline or amorphous.

Another metal element as referred to herein indicates a constituent element of the support to be described later, a third constituent element contained in the catalyst in addition to the oxidized nickel and X, or a metal component such as an alkaline metal, alkaline earth metal or rare earth metal.

The catalyst according to the present embodiment has oxidized nickel and X loaded onto a support as previously described, and preferably demonstrates superior effects by forming composite nanoparticles composed of oxidized nickel and X. Furthermore, the composite nanoparticle as referred to in the present embodiment refers to a particle on the nano level containing different binary metal species within a single particle. Although examples of different binary metal species may include binary metal particles in which both the nickel and X components are metals, and metal particles in which an alloy or intermetallic compound of nickel and X is formed, in the case of using these as catalysts for producing carboxylic acid ester, selectivity and catalyst activity of the target product are low as compared with the catalyst according to the present invention, thereby making them undesirable.

The catalyst according to the present embodiment preferably comprises oxidized nickel on the support independently in addition to the composite nanoparticles composed of oxidized nickel and X. The presence of oxidized nickel not compounded with X serves to further enhance the structural stability of the catalyst particles, as well as inhibit increases in pore diameter caused by long-term reactions and the accompanying growth of the composite nanoparticles. This effect is remarkable in the case of using an aluminum-containing silica-based composition containing silica and aluminum or a silica-alumina-magnesia composition for the support as will be described later.

The following provides an explanation of the action by which structural stability of catalyst particles is enhanced and increases in pore diameter caused by long-term reactions along with accompanying growth of composite nanoparticles are inhibited due to the presence of free oxidized nickel on the support.

As will be described later, the production of acetals and the like attributable to acidic substances, represented by-products characteristic to reactions for producing carboxylic acid esters, methacrylic acid or acrylic acid, can be inhibited by maintaining the pH of the reaction system to 6 to 9, and more preferably to neutral conditions (such as pH 6.5 to 7.5), or in other words by maintaining at a pH as close to pH 7 as possible, by adding a compound of an alkaline metal or alkaline earth metal to the reaction system.

According to studies conducted by the inventors of the present invention, in the case of carrying out a long-term reaction according to the procedure described above using a catalyst in which single component gold nanoparticles are loaded onto a support of the present embodiment, the catalyst particles were determined to gradually undergo structural changes. This phenomenon is thought to be the result of the catalyst particles repeatedly being locally exposed to acid and base due to the reaction procedure described above, thereby causing a portion of the Al in the support to be dissolved and precipitate resulting in rearrangement of the silica-alumina crosslinked structure, which in turn causes an increase in the pore diameter of the catalyst particles. In addition, simultaneous to the increase in pore diameter, particle growth is promoted by sintering of the gold particles, which was determined to lower catalyst activity.

On the other hand, the presence of composite nanoparticles and oxidized nickel alone on the support served to enhance the structural stability of the catalyst particles due to the procedure described above, while also inhibiting increases in pore diameter and growth of the composite nanoparticles. As was previously described, the reason for this is thought to be that the reaction between oxidized nickel and constituent elements of the support results in the formation of nickel oxide compounds or composite oxides containing nickel such as solution solutions, and as a result of such nickel compounds acting to stabilize the silica-alumina crosslinked structure, structural stability of the catalyst particles is greatly improved. The performance of such catalyst structural stabilizing effects is presumed by the inventors of the present invention to be attributable to the oxidized nickel present in the support. Consequently, these effects are naturally obtained in the case oxidized nickel contained in the composite nanoparticles is in contact with the support, and maximum stabilizing effects are thought to be obtained if free oxidized nickel is present on the support.

[Support]

There are no particular limitations on the support of the catalyst for producing carboxylic acid ester according to the present embodiment provided it is capable of being loaded with oxidized nickel and X, and a catalyst support of the prior art used for carboxylic acid ester synthesis can be used.

Examples of this support may include various types of supports such as activated carbon, silica, alumina, silica-alumina, titania, silica-titania, zirconia, magnesia, silica-magnesia, silica-alumina-magnesia, calcium carbonate, zinc oxide, zeolite and crystalline metallosilicate. Preferable examples thereof may include activated carbon, silica, alumina, silica-alumina, silica-magnesia, silica-alumina-magnesia, titania, silica-titania and zirconia. More preferable examples may include silica-alumina and silica-alumina-magnesia.

In addition, a single or plurality of types of metal components selected from the group consisting of alkaline metals (Li, Na, K, Rb, Cs), alkaline earth metals (Be, Mg, Ca, Sr, Ba) and rare earth metals (La, Ce, Pr) may also be contained in the support. A loaded metal component is preferably an oxide obtained by firing, for example, a nitrate or acetate.

An aluminum-containing silica-based composition comprising silica and aluminum or a silica-alumina-magnesia composition is preferably used for the support. This type of support has higher water resistance than silica and higher acid resistance than alumina. In addition, it is also provided with superior physical properties as compared with supports typically used in the prior art, including being harder and having greater mechanical strength than activated carbon, while also allowing the stable loading of oxidized nickel and X which are catalyst active components (wherein X represents at least one element selected from the group consisting of nickel, palladium, platinum, ruthenium, gold, silver and copper). Consequently, the catalyst is able to maintain a high level of reactivity over a long period of time.

A catalyst for producing carboxylic acid ester, in which oxidized nickel and X have a specific atomic ratio, and an aluminum-containing silica-based composition or silica-alumina-magnesia composition is used for the support, demonstrates high mechanical strength and physical stability while having a high surface area suitable for use as a catalyst support, and also satisfies corrosion resistance with respect to the characteristic liquid nature of the reaction in the form of a carboxylic acid ester synthesis reaction in the presence of oxygen.

The following provides an explanation of the properties of the support of the present embodiment that enables considerable improvement of catalyst life. The reason for having been able to significantly improve the mechanical strength and chemical stability of the support is presumed to be as follows.

In an aluminum-containing silica-based support, Si—O—Al—O—Si bonds are newly formed by adding aluminum (Al) to non-crosslinked silica (Si—O) chains of silica gel. Since Al-crosslinked structures are formed without losing the inherent stability of Si—O chains with respect to acidic substances, Si—O bonds are strengthened and hydrolysis stability (hereinafter simply referred to as "water resistance") is thought to be significantly improved. In addition, when Si—O—Al—O—Si crosslinked structures are formed, the number of non-crosslinked Si—O chains decreases as compared with silica gel alone, which is thought to result in an increase in mechanical strength as well. Namely, the amount of Si—O—Al—O—Si structures formed is presumed to correlate with improvement of mechanical strength and water resistance of the resulting silica gel.

In a silica-aluminum-magnesia support, as a result of magnesia being present in addition to silica and alumina, charge stabilization is promoted as a result of compensatory neutralization by Mg (divalent) of differences in charge resulting from differences in the valences between Si (tetravalent) and Al (trivalent) caused by the formation of Si—O—Al—O—Si crosslinked structures. Moreover, since charge balance is obtained through the use of a three-component system, structural stability is presumed to be further enhanced. Consequently, in contrast to a silica-alumina support alone demonstrating acidity, a support containing silica, alumina and magnesia is nearly neutral, and this is thought to lead to inhibition of prominent acetal formation under acidic conditions.

One reason for it being possible to stably load oxidized nickel and X onto a support for a long period of time is that the mechanical strength and chemical stability of the support are significantly improved as described above, thus providing the support with superior physical properties in comparison with supports typically used in the prior art. As a result, nickel and X which are the catalyst active components are resistant to exfoliation, thus enabling them to be stably loaded over a long period of time.

The nickel component of commonly used supports, such as silica or silica-alumina, has been observed to gradually elute over the course of long-term reactions. In contrast, in the case of using the above-mentioned support, the inventors of the present invention found that elution of nickel component is inhibited over a long period of time. On the basis of the results of X-ray photoelectron spectroscopy (XPS), transmission electron microscopy (TEM/EDX) and high-resolution X-ray fluorescence (HRXRF), in the case of using a silica or silica-titania support, the eluting nickel component was confirmed to be nickel oxide present alone on the support. Since nickel oxide is a soluble compound in acid, it is presumed to be eluted by characteristic by-products of this reaction in the form of acidic substances represented by methacrylic acid and acrylic acid.

On the basis of analysis of the chemical state of nickel by high-resolution X-ray fluorescence (HRXRF), the nickel of the catalyst according to the present embodiment is presumed to not only be nickel oxide which is a single compound, but also be present due to the formation of composite oxides containing nickel, such as a nickel oxide compounds, solid solutions or mixture thereof, formed by bonding between nickel and a constituent element of the support.

High-resolution X-ray fluorescence (HRXRF) analysis makes it possible to analyze chemical state based on energy locations (chemical shifts) and the shape of the resulting spectrum due to its extremely high energy resolution. In the case of the K spectra of 3d transition metal elements in particular, changes occur in chemical shift and shape due to changes in valence and electronic state, and the chemical state can be analyzed in detail. In the catalyst according to the present embodiment, changes occurred in the Ni K spectrum, thus confirming that the chemical state of nickel differs from nickel oxide which is a single compound.

For example, nickel aluminate, which is formed from nickel oxide and alumina, is a compound that is insoluble in acid. As a result of forming such a nickel compound on a support, elution of the nickel component is presumed to be improved considerably.

The following provides an explanation of two preferable supports for significantly improving the life of the catalyst according to the present embodiment, namely a support containing silica and alumina and a silica-alumina-magnesia support.

The elementary composition of a support containing silica and alumina is such that the amount of aluminum is from 1 to 30 mol %, preferably from 5 to 30 mol % and more preferably from 5 to 25 mol % based on the total molar amount of silicon and aluminum. If the amount of aluminum is within this range, acid resistance and mechanical strength tend to be favorable.

In addition, the further containing of at least one type of basic metal component selected from the group consisting of alkaline metals, alkaline earth metals and rare earth metals in the support of the catalyst according to the present embodiment in addition to silica and alumina is preferable from the viewpoint of further improving mechanical strength and chemical stability. Examples of alkaline metals of this basic metal component may include Li, Na, K, Rb and Cs, examples of alkaline earth metals may include Be, Mg, Ca, Sr and Ba, and examples of rare earth metals may include La, Ce and Pr.

The elementary composition of a support containing silica, alumina and at least one type of basic metal component selected from the group consisting of alkaline metals, alkaline earth metals and rare earth metals is such that the amount of aluminum is within a range of from 1 to 30 mol %, preferably from 5 to 30 mol % and more preferably from 5 to 25 mol % based on the total molar amount of silicon and aluminum. In addition, the composition ratio of the basic metal component and alumina in terms of the atomic ratio of (alkaline metal+½×alkaline earth metal+⅓×rare earth metal)/Al is preferably within a range of from 0.5 to 10, more preferably from 0.5 to 5.0 and even more preferably from 0.5 to 2.0. If the elementary composition of silica, alumina and basic metal component is within the above range, the silicon, aluminum and basic metal element form a specific stable bonded structure, and as a result, the mechanical strength and water resistance of the support tend to be favorable.

Moreover, a support containing silica, alumina and magnesia preferably comprises from 42 to 90 mol % of silicon, from 5.5 to 38 mol % of aluminum and from 4 to 38 mol % of magnesium, and more preferably from 75 to 90 mol % of silicon, from 5.5 to 15 mol % of alumina and from 4 to 10 mol % of magnesia based on the total molar amount of silicon, aluminum and magnesium from the viewpoint of mechanical strength and water resistance of the support. This is presumed to be because the silicon, aluminum and magnesium form a specific stable bonded structure if within these ranges.

The following provides an explanation of a process for preparing the two preferable types of supports used in the present embodiment having the compositions described above.

There are no particular limitations on the processed used to prepare a support containing silica and alumina, and an aluminum-containing silica-based composition obtained according to, for example, the processes of (1) to (5) below can be prepared by firing under conditions to be described later.

(1) Use of a commercially available silica-alumina composition.
(2) Reaction of a silica sol with an aluminum compound solution.
(3) Reaction of a silica sol with an aluminum composition insoluble in water.
(4) Reaction of a silica gel with an aqueous solution of a water-soluble aluminum compound.
(5) Solid-phase reaction of a silica gel and an aluminum compound.

The following provides a detailed explanation of the processes for preparing a support indicated in (2) to (5) above.

In the processes of (2) to (5) above, a silica sol or silica gel is used for the silica source. There are no particular limitations on the length of the Si—O chain of the silica gel provided it has non-crosslinked Si sites that react with Al. Although preferable examples of aluminum compounds may include water-soluble compounds such as sodium aluminate, aluminum chloride hexahydrate, aluminum perchlorate hexahydrate, aluminum sulfate, aluminum nitrate nonahydrate or aluminum diacetate, insoluble compounds such as aluminum hydroxide or aluminum oxide can also be used provided they are compounds that react with non-crosslinked Si in the silica sol or silica gel.

In the case of using the processes of (2) and (3) that use a silica sol for the starting material, the silica sol is mixed with an aluminum compound to obtain a mixed sol containing silica sol and aluminum compound, followed by carrying out a hydrothermal reaction for 1 to 48 hours at 20 to 100° C. and drying to obtain a gel, and then firing under the temperature, time and atmospheric conditions to be described later. Alternatively, an alkaline aqueous solution is added to the above-mentioned mixed sol to co-precipitate silica and an aluminum compound, followed by drying and then firing under conditions to be described later. In addition, the above-mentioned mixed sol can be converted into fine particles directly using a spray dryer, or the mixed sol can be dried to form a gel and then granulated to obtain a support containing silica and aluminum having desired particle diameters.

In the case of the process of (3) in particular, although a silica sol is reacted with an aluminum compound that is insoluble in water, at this time the aluminum compound can be crushed to a prescribed particle size in advance or preliminarily coarsely crushed. After having mixed and reacted the silica sol and the water-insoluble aluminum compound, the mixture is dried followed by firing under conditions to be described later. The silica-alumina compound may be crushed to a prescribed particle size after firing without crushing the aluminum compound in advance.

In the case of the process of (4) in which a silica gel is used for the starting material, an aqueous solution of a water-soluble aluminum compound is reacted in silica gel, and the silica gel may either be crushed to a prescribed particle size in advance or preliminarily coarsely crushed. After mixing and reacting the silica gel and aqueous solution of a water-soluble aluminum compound for 1 to 48 hours at 20 to 100° C., the mixture is dried followed by firing for 1 to 48 hours under the conditions to be described later. The silica-alumina compound may be crushed to a prescribed particle size after firing without crushing the silica gel in advance.

Similarly, in the process of (5) that also uses a silica gel for the starting material, a mixture is prepared by reacting the silica gel with an aluminum compound in the solid phase. The Al is reacted in the solid phase with non-crosslinked Si. The silica gel and aluminum compound may be crushed to a prescribed particle size in advance, or may be preliminarily coarsely crushed. Crushing may be carried out independently for each substance or both substances may be crushed after mixing. Firing is carried out under temperature, time and atmospheric conditions to be described later. The mixture of silica gel and aluminum compound can be used by crushing to a desired particle size after the reaction without crushing in advance.

With respect to a process for preparing a support containing silica, alumina and at least one type of basic metal component selected from the group consisting of alkaline metals, alkaline earth metals and rare earth metals, the support can be prepared by drying a slurry comprising a mixture of silica, alumina and an alkaline metal compound, alkaline earth metal compound and/or rare earth metal compound in accordance with process for preparing a support containing silica and alumina as described above, followed by firing under the conditions to be described later.

Typical commercially available compounds similar to the aluminum raw material can be used for the raw material of the alkaline metal, alkaline earth metal and rare earth metal. The raw material is preferably a water-soluble compound, and more preferably a hydroxide, carbonate, sulfate or acetate.

Another example of a preparation process that can be used may include adsorbing a basic metal component selected from the group consisting of alkaline metals, alkaline earth metals and rare earth metals onto a support containing silica and alumina. For example, an immersion process, in which a support is added to a solution in which a basic metal compound has been dissolved followed by heat treatment, or an impregnation process, in which an amount of a basic compound equal to pore volume is incorporated into a support followed by drying treatment, can be applied. However, a process in which an alkaline metal compound is adsorbed later requires caution in that liquid drying treatment is carried out under mild conditions in consideration of highly dispersing the basic metal component on the support.

Next, an explanation is provided of a process for preparing a support containing silica, alumina and magnesia. A silica-alumina-magnesia support obtained according to the processes of (1) to (5) below, for example, can be prepared by firing under conditions to be described later.
(1) Preliminary formation of a silica-alumina gel followed by the addition of magnesia.
(2) Reaction of a silica sol, aluminum compound and magnesium compound.
(3) Reaction of a silica sol, water-insoluble aluminum compound and water-insoluble magnesium compound.
(4) Reaction of a silica gel, water-soluble aluminum compound and water-soluble magnesium compound.
(5) Solid phase reaction of a silica gel, aluminum compound and magnesium compound.

In the processes of (1) to (5) above, a silica sol, water glass or silica gel is used for the silica source. There are no particular limitations on the length of the Si—O chain of the silica gel provided it has non-crosslinked Si sites that react with Al. Although preferable examples of aluminum compounds may include water-soluble compounds such as sodium aluminate, aluminum chloride hexahydrate, aluminum perchlorate hexahydrate, aluminum sulfate, aluminum nitrate nonahydrate or aluminum diacetate, insoluble compounds such as aluminum hydroxide or aluminum oxide can also be used provided they are compounds that react with non-crosslinked Si in the silica sol or silica gel. Examples of magnesium compounds that can be used may include magnesium oxide, magnesium hydroxide, magnesium acetate, magnesium nitrate, magnesium chloride and magnesium sulfate.

In the case of the process of (1) in which silica-alumina gel is used for the raw material, sulfuric acid first added to water glass to prepare a silica hydrogel having a pH of from 8 to 10.5, followed by the addition of an $Al_2(SO_4)_3$ solution thereto (pH 2 or lower) and the addition of sodium aluminate (pH 5 to 5.5) to prepare a silica-alumina hydrogel. Next, the moisture content of the gel is then adjusted to 10 to 40% by spray drying and the like followed by the addition of magnesia, carrying out a hydrothermal reaction for 1 to 5 hours at 50 to 90° C., drying and then firing under conditions to be described later to obtain a support.

In the case of the processes of (2) and (3) that use a silica sol for the starting material, a silica sol, aluminum compound and magnesium compound are mixed to obtain a mixed sol containing the silica sol, aluminum compound and magnesium compound, and a hydrothermal reaction is carried out for 1 to 48 hours at 20 to 100° C. followed by drying to obtain a gel, after which the gel is fired under temperature, time and atmospheric conditions to be described later. Alternatively, an alkaline aqueous solution is added, an alkaline aqueous solution is added to the above-mentioned mixed sol to coprecipitate silica, an aluminum compound and a magnesium compound, followed by drying and then firing under conditions to be described later. In addition, the above-mentioned mixed sol can be converted into fine particles directly using a spray dryer, or the mixed sol can be dried to form a gel and then granulated to obtain a support containing silica, aluminum, magnesia having desired particle diameters.

In the case of the process of (3) in particular, although a silica sol is reacted with an aluminum compound and magnesium compound that are insoluble in water, at this time the aluminum compound and magnesium compound can be crushed to a prescribed particle size in advance or preliminarily coarsely crushed. After having mixed and reacted the silica sol, the water-insoluble aluminum compound and the water-insoluble magnesium compound, the mixture is dried followed by firing under conditions to be described later. The silica-alumina-magnesia compound may be crushed to a prescribed particle size after firing without crushing the aluminum compound and magnesium compound in advance.

The process of (4) using a silica gel for the starting material, an aqueous solution of a water-soluble aluminum compound and water-soluble magnesium compound is reacted in silica gel, and the silica gel may either be crushed to a prescribed particle size in advance or preliminarily coarsely crushed. After mixing and reacting the silica gel and aqueous solution of the water-soluble aluminum compound and water-soluble magnesium compound for 1 to 48 hours at 20 to 100° C., the mixture is dried followed by firing for 1 to 48 hours under the conditions to be described later. The silica-alumina-magnesia compound may be crushed to a prescribed particle size after firing without crushing the silica gel in advance.

Similarly, in the process of (5) that also uses a silica gel for the starting material, a mixture is prepared by reacting the silica gel with an aluminum compound and a magnesium compound in the solid phase. The silica gel, aluminum compound and magnesium compound may be crushed to a prescribed particle size in advance, or may be preliminarily coarsely crushed. Crushing may be carried out independently for each substance or all three substances may be crushed after mixing. Firing is carried out under temperature, time and atmospheric conditions to be described later. The mixture of silica gel, aluminum compound and magnesium compound can be used by crushing to a desired particle size after the reaction without crushing in advance.

In addition, inorganic and organic substances can be added to a mixed slurry of each of the above raw materials to control slurry properties or finely adjust properties such as the pore structure of the product or the properties of the resulting support.

Specific examples of inorganic substances used may include inorganic acids such as nitric acid, hydrochloric acid or sulfuric acid, metal salts of alkaline metals such as Li, Na, K, Rb or Cs or alkaline earth metals such as Mg, Ca, Sr or Ba, water-soluble compounds such as ammonia or ammonium sulfate, and clay minerals that form suspensions by dispersing in water. In addition, specific examples of organic substances may include polymers such as polyethylene glycol, methyl cellulose, polyvinyl alcohol, polyacrylic acid or polyacrylamide.

Although there are various effects of the addition or inorganic and organic substances, these effects may mainly include forming a spherical support as well as controlling pore diameter and pore volume, and more specifically, the liquid properties of the mixed slurry are an important factor in obtaining a spherical support. Liquid properties can be changed to those that facilitate the obtaining of a spherical support by adjusting the viscosity and solid concentration with an inorganic or organic substance. In addition, control of pore diameter and pore volume can be carried out by selecting the optimum organic compound that remains within the support in the formation stage and can be removed by firing and washing procedures following formation.

A support can be prepared by spray drying a mixed slurry of each of the above-mentioned raw materials and additives. A known spraying apparatus, such as the rotating disc type, dual liquid nozzle type or pressurized nozzle type can be used to liquefy the mixed slurry.

The sprayed liquid is required to be used in a well-mixed state. If the liquid is poorly mixed, the liquid affects the performance of the support, such as by causing a decrease in durability due to uneven distribution of the composition. When formulating raw materials in particular, since there are cases of the occurrence of increases in slurry viscosity or partial gelation (colloid condensation), there is concern over the formation of non-uniform particles. Consequently, there are cases in which it is preferable to control a silica sol of around pH 2 to a semi-stable range, for example, by employing a method such as adding acid or base while also taking additional considerations such as gradually mixing the raw materials while stirring.

It is necessary for the sprayed liquid to have a certain degree of viscosity and solid concentration. If viscosity and solid concentration are excessively low, many of the porous bodies obtained by spray drying are in the form of distorted spheres rather than perfect spheres. In addition, if viscosity and solid concentration are excessively high, in addition to having a detrimental effect on the dispersibility of the porous bodies, it is not possible to form stable droplets depending on the liquid properties. Consequently, viscosity is preferably within a range of from 5 to 10000 cps provided the liquid can be sprayed at that viscosity, and a higher sprayable viscosity tends to be preferable with respect to shape, and based on the balance between viscosity and ease of manipulation, viscosity is preferably selected from within a range of from 10 to 1000 cp. In addition, a solid concentration within the range of from 10 to 50% by mass is preferable from the viewpoints of shape and particle diameter. Furthermore, a hot air temperature at the drying column inlet of the spray dryer of from 200 to 280° C. and a drying column outlet temperature within a range of from 110 to 140° C. are preferable as general indicators of spray drying conditions.

The support firing temperature is typically selected from within a range of from 200 to 800° C. Sintering at a temperature above 800° C. causes a remarkable decrease in specific surface area, thereby making this undesirable. In addition, although there are no particular limitations on the firing atmosphere, firing is typically carried out in air or nitrogen. In addition, although firing time can be determined depending on the specific surface area after firing, it is typically from 1 to 48 hours. Since support physical properties such as porosity change, it is necessary to select suitable temperature and heating conditions for the firing conditions. If the firing temperature is excessively low, it becomes difficult to maintain durability as a composite oxide, while if the firing temperature is excessively high, a decrease in pore volume results. In addition, heating conditions preferably may include gradually raising the temperature by using programmed heating and the like. In the case of firing under conditions such that the temperature rises rapidly, gasification and combustion of inorganic and organic substances becomes violent, causing them to be exposed to temperatures above the set temperature or causing pulverization, thereby making this undesirable.

The specific surface area of the support, as measured using the BET nitrogen adsorption method, is preferably 10 $m^2/g$ or more, more preferably 20 $m^2/g$ or more and even more preferably 50 $m^2/g$ or more, from the viewpoints of ease of loading composite nanoparticles, catalytic activity and resistance to exfoliation. In addition, although not particularly required from the viewpoint of catalyst activity, the specific surface area of the support is preferably 700 $m^2/g$ or less, more preferably 350 $m^2/g$ or less and even more preferably 300 $m^2/g$ or less, from the viewpoints of mechanical strength and durability.

The pore structure of the support is an extremely important physical property with respect to loading properties of metal components other than strength, long-term stability including exfoliation, and reaction properties, and pore diameter is a physical value required for demonstrating these properties. If pore diameter is less than 3 nm, although exfoliation properties of the loaded metal are favorable, in the case of using the catalyst in a liquid phase reaction and the like, pore diameter is preferably 3 nm or more, from the viewpoint of maintaining high reactivity without making intrapore diffusion resistance excessively large so that the diffusion step of the reaction substrate is not the limiting step. On the other hand, the pore diameter is preferably 50 nm or less, from the viewpoint of resistance of the catalyst to cracking and resistance to exfoliation of loaded metal. Thus, the pore diameter is preferably from 3 to 50 nm, and more preferably from 3 to 30 nm. Pore volume is required to allow the presence of pores for loading the composite nanoparticles. However, if pore volume becomes excessively large, strength tends to decrease rapidly. Thus, a pore volume within a range of from 0.1 to 1.0 mL/g is preferable, while that within the range of from 0.1 to 0.5 mL/g is more preferable, from the viewpoint of strength. The support of the present embodiment preferably satisfies the above ranges for pore diameter and pore volume.

The shape of the support is selected from among a hollow cylindrical shape or honeycomb shape being a structure that demonstrates low pressure loss in a fixed bed according to the type of reaction, and under liquid phase slurry suspension conditions, the slurry is typically spherical and the shape of the support is selected that allows the support to be used by selecting the optimum pore diameter based on the reactivity and separation method. For example, in the case of employing a catalyst separation process using the typically simple method of precipitation separation, a particle diameter of from 10 to 200 μm is preferably selected, that of from 20 to 150 μm is more preferably selected, and that of from 30 to 150 μm is even more preferably selected based on the balance with reaction properties. In the case of employing a cross filter method, small particles having a particle diameter of from 0.1 to 20 μm or less are preferable due to their high reactivity. The catalyst for producing carboxylic acid ester according to the present embodiment can thus be used by changing the type and form of support according to the purpose of use.

Although there are no particular limitations on the amount of oxidized nickel loaded onto the support, it is generally from 0.1 to 20% by mass, preferably from 0.2 to 10% by mass, more preferably from 0.2 to 5% by mass and even more preferably from 0.5 to 2% by mass as nickel based on the support weight. The amount of X loaded onto the support is generally from 0.1 to 10% by mass, preferably from 0.2 to 5% by mass, more preferably from 0.2 to 2% by mass, even more preferably from 0.3 to 1.5% by mass and particularly preferably from 0.5 to 1.0% by mass as metal based on the support weight.

Moreover, in the present embodiment, a preferable range exists for the atomic ratio between nickel and the elementary composition of the support. In the case of using a support of the present embodiment containing silica and alumina, the composition ratio of nickel and alumina in the catalyst in terms of the atomic ratio of Ni/Al is preferably from 0.01 to 1.0, more preferably from 0.02 to 0.8 and even more preferably from 0.04 to 0.6. In addition, in the case of using a support containing silica, alumina and at least one type of basic metal component selected from the group consisting of alkaline metals, alkaline earth metals and rare earth metals, the composition ratio of nickel and alumina in the catalyst in terms of the atomic ratio of Ni/Al is preferably from 0.01 to 1.0, more preferably from 0.02 to 0.8 and even more preferably from 0.04 to 0.6, while the composition ratio of nickel and basic metal component in terms of the atomic ratio of Ni/(alkaline metal+alkaline earth metal+rare earth metal) is preferably from 0.01 to 1.2, more preferably from 0.02 to 1.0 and even more preferably from 0.04 to 0.6.

Moreover, preferable ranges also exist for the atomic ratio between nickel and the support constituent elements of aluminum and magnesium in the case of a silica-alumina-magnesia support. The composition ratio of nickel and alumina in the catalyst in terms of the atomic ratio of Ni/Al is preferably from 0.01 to 1.0, more preferably from 0.02 to 0.8 and even more preferably from 0.04 to 0.6. In addition, the composition ratio of nickel and magnesium in terms of the atomic ratio of Ni/Mg is preferably from 0.01 to 1.2, more preferably from 0.02 to 1.0 and even more preferably from 0.04 to 0.6.

If the atomic ratio of nickel and aluminum which is a support constituent element, basic metal element or magnesium is within the above ranges, effects resulting in improvement of elution of nickel and structural changes in the catalyst particles tend to be enhanced. This is thought to be the result of the nickel, aluminum, basic metal component and magnesium forming a specific composite oxide when being within these ranges, thereby forming a stable bonded structure.

The catalyst for use in production of carboxylic acid ester according to the present embodiment can also comprise a third constituent element as a catalyst active component in addition to the oxidized nickel and X. Examples of elements that can be contained may include titanium, vanadium, chromium, manganese, iron, cobalt, zinc, gallium, zirconium, niobium, molybdenum, rhodium, cadmium, indium, tin, antimony, tellurium, hafnium, tantalum, tungsten, rhenium, osmium, iridium, mercury, thallium, lead, bismuth, aluminum, boron, silicon and phosphorous. The content of these third constituent elements is from 0.01 to 20% by mass and preferably from 0.05 to 10% by mass per catalyst. In addition, at least one type of metal component selected from the group consisting of alkaline metals, alkaline earth metals and rare earth metals may also be contained in the catalyst. The content of these alkaline metals, alkaline earth metals or rare earth metals is selected from within a range of 15% by mass or less per catalyst.

Note that these third constituent elements or alkaline metals, alkaline earth metals and rare earth metals may be contained in the catalyst during production and reaction of the catalyst, or a method may be used by which they are contained in the support in advance.

[Catalyst Shape]

The specific surface area of the catalyst according to the present embodiment, as measured using the BET nitrogen adsorption method, is preferably within a range of from 20 to 350 $m^2/g$, more preferably from 50 to 300 $m^2/g$ and even more preferably from 100 to 250 $m^2/g$, from the viewpoints of catalytic activity and resistance to exfoliation of active components.

The pore structure of the catalyst is an extremely important physical property with respect to loading properties of metal components, long-term stability including exfoliation, and reaction properties, and pore diameter is a physical value required for demonstrating these properties. If pore diameter is less than 3 nm, although exfoliation properties of the loaded metal are favorable, in the case of using the catalyst in a liquid phase reaction and the like, pore diameter is preferably 3 nm or more, from the viewpoint of maintaining high reactivity without making intrapore diffusion resistance excessively large so that the diffusion step of the reaction substrate is not the limiting step. On the other hand, the pore diameter is preferably 50 nm or less, from the viewpoint of resistance of the catalyst to cracking and resistance to exfoliation of loaded metal. Thus, the pore diameter is preferably from 3 to 50 nm, more preferably from 3 to 30 nm and even more preferably from 3 to 10 nm. Pore volume is preferably within a range of from 0.1 to 1.0 mL/g, more preferably from 0.1 to 0.5 mL/g and even more preferably from 0.1 to 0.3 mL/g, from the viewpoints of loading properties and reaction properties. The catalyst according to the present embodiment preferably satisfies the above ranges for pore diameter and pore volume.

Catalyst pore diameter can be suitably selected depending on the type of reaction. For example, when using in a liquid phase suspended state, for example, pore diameter varies according to the method used to separate the catalyst, and in the case of separation by spontaneous settling, is preferably from 10 to 200 μm, more preferably from 20 to 150 μm and even more preferably from 20 to 100 μm.

[Process for Producing Catalyst for Use in Production of Carboxylic Acid Ester]

There are no particular limitations on the production process of the catalyst according to the present embodiment provided a catalyst as previously described is obtained, and a commonly used production process for a loading catalyst can be applied, examples of which may include impregnation processes (such as adsorption, pore filling, evaporation to dryness or spraying), precipitation processes (such as co-precipitation, precipitation deposition or kneading), ion exchange and vapor deposition. In the present embodiment, impregnation and precipitation processes are preferable, while precipitation processes are used more preferably.

The following provides an explanation of a typical process for preparing the catalyst according to the present embodiment using the example of precipitation. In a first step, for example, a catalyst precursor is obtained by precipitating nickel and component X on a support by neutralizing an acidic aqueous solution of a soluble metal salt containing nickel and X. At this stage, the nickel and X components (such as a hydroxide) are precipitated and fixed on the support due to neutralization reaction between nickel and X ions in the aqueous solution. Compounding of nickel and component X is preferably made to be more adequate by simultaneously precipitating from a mixed aqueous solution of both components.

Next, in a second step, the catalyst according to the present embodiment can be obtained by rinsing and drying the catalyst precursor obtained in the first step as necessary followed by heat treatment.

Examples of soluble metal salts containing nickel used to prepare the catalyst may include nickel nitrate, nickel acetate and nickel chloride. In addition, examples of soluble metal salts containing X may include palladium chloride and palladium acetate in the case palladium is selected for X, ruthenium chloride and ruthenium nitrate in the case ruthenium is selected for X, chloroauric acid, sodium tetrachloroaurate, potassium dicyanoaurate, gold diethylamine trichloride and gold cyanide in the case gold is selected for X, and silver chloride and silver nitrate in the case silver is selected for X.

Examples of bases used to prepare the catalyst may include sodium hydroxide, potassium hydroxide, sodium carbonate, potassium carbonate and ammonia. In addition, one or a plurality of types of basic metal components selected from the group consisting of alkaline metals (such as Li, Na, K, Rb or Cs), alkaline earth metals (such as Be, Mg, Ca, Sr or Ba) and rare earth metals (such as La, Ce or Pr) may be contained in the support.

In the first step, an acid aqueous solution of a soluble metal salt containing nickel and X is mixed with a support and then neutralized with base while stirring to precipitate a precipitate of nickel and component X onto a support. Conditions such as the concentration of the aqueous solution containing nickel and X, base, pH of the aqueous solution and temperature are suitably selected during precipitation of the nickel and component X.

The each concentration of the aqueous solution containing nickel and X is generally within a range of from 0.0001 to 1.0 mol/L, preferably from 0.001 to 0.5 mol/L and more preferably from 0.005 to 0.2 mol/L. The ratio of nickel and X in the aqueous solution in terms of the atomic ratio of Ni/X is preferably within a range of from 0.1 to 10, more preferably from 0.2 to 5.0 and even more preferably from 0.5 to 3.0.

In addition, the pH of the aqueous solution is adjusted with the above-mentioned base so as to generally be within a range of from 5 to 10 and preferably within a range of from 6 to 8. The temperature of the aqueous solution is generally within a range of from 0 to 100° C., preferably from 30 to 90° C. and more preferably from 60 to 90° C.

In addition, there are no particular limitations on the amount of time during precipitation of nickel and component X, and although this time differs depending on such factors as the loaded species, amounts of nickel and X loaded and the ratio of nickel and X, it is generally within a range of from 1 minute to 5 hours, preferably from 5 minutes to 3 hours and more preferably from 5 minutes to 1 hour.

The temperature during heat treatment of the catalyst precursor in the second step is generally from 40 to 900° C., preferably from 80 to 800° C., more preferably from 200 to 700° C. and even more preferably from 300 to 600° C. Heat treatment is carried out in an atmosphere such as air (or atmospheric air), oxidizing atmosphere (such as oxygen, ozone, nitrogen oxide, carbon dioxide, hydrogen peroxide, hypochlorous acid or inorganic/organic peroxide) or inert gas atmosphere (such as helium, argon or nitrogen). The duration of heat treatment is suitably selected according to the heat treatment temperature and amount of catalyst precursor.

Following the above-mentioned second step, reducing treatment can be carried out in a reducing atmosphere as necessary (such as hydrogen, hydrazine, formalin or formic acid). In this case, reduction is carried out by selecting a treatment method in which the oxidized nickel is not completely reduced to a metal state. The temperature and duration of reducing treatment are suitably selected according to the type of reducing agent, type of X and amount of catalyst.

Moreover, oxidizing treatment can also be carried out as necessary in air (or atmospheric air) or an oxidizing atmosphere (such as oxygen, ozone, nitrogen oxide, carbon dioxide, hydrogen peroxide, hypochlorous acid or inorganic/organic peroxide) following the heat treatment or reducing treatment as described above.

A third constituent element in addition to the nickel and X can be added during catalyst preparation or under the reaction conditions. Alkaline metal, alkaline earth metal or rare earth metal may also be added during catalyst preparation or to the reaction system. In addition, raw materials of the third constituent element, alkaline metal, alkaline earth metal and rare earth metal are selected from salts of organic acids, salts of inorganic acids, hydroxides and the like.

[Process for Producing Carboxylic Acid Ester]

Carboxylic acid ester can be produced from (a) aldehyde and alcohol or (b) one or more types of alcohols in the presence of oxygen using the catalyst for use in production of carboxylic acid ester according to the present embodiment.

Although there are no particular limitations on the amount of catalyst used, and can be varied over a wide range according to, for example, the types of reaction raw materials, catalyst composition and preparation method, reaction conditions or type of reaction, in the case of reacting the catalyst in the state of a slurry, the catalyst can be preferably used such that the solid concentration in the slurry is within a range of from 1 to 50 wt/vol %, preferably from 3 to 30 wt/vol % and more preferably from 10 to 25 wt/vol %.

Examples of aldehydes able to be used as raw materials may include $C_1$ to $C_{10}$ aliphatic saturated aldehydes such as formaldehyde, acetaldehyde, propionaldehyde, isobutyrylaldehyde or glyoxal; $C_3$ to $C_{10}$ aliphatic α•β-unsaturated aldehydes such as acrolein, methacrolein or crotonaldehyde; $C_6$ to $C_{20}$ aromatic aldehydes such as benzaldehyde, tolylaldehyde, benzylaldehyde or phthalaldehyde; and derivatives of these aldehydes. These aldehydes can be used alone or as a mixture of any two or more types thereof.

Examples of alcohols able to be used may include $C_1$ to $C_{10}$ aliphatic saturated alcohols such as methanol, ethanol, isopropanol, butanol, 2-ethylhexanol or octanoyl; $C_5$ to $C_{10}$ alicyclic alcohols such as cyclopentanol or cyclohexanol; $C_2$ to $C_{10}$ diols such as ethylene glycol, propylene glycol or butanediol; $C_3$ to $C_{10}$ aliphatic unsaturated alcohols such as allyl alcohol or methallyl alcohol; $C_6$ to $C_{20}$ aromatic alcohols such as benzyl alcohol; and hydroxyoxetanes such as 3-alkyl-3-hydroxymethyloxetane. These alcohols can be used alone or in the form of a mixture of any two or more types thereof.

In the production process according to the present embodiment, (a) a corresponding carboxylic acid ester can be produced by reacting aldehyde and alcohol, or (b) a corresponding carboxylic acid ester can be produced by reacting one or more types of alcohols.

In the case of producing carboxylic acid ester from aldehyde and alcohol, there are no particular limitations on the weight ratio of the aldehyde and alcohol, and although production can be carried out over a wide range of weight ratios, such as a molar ratio of aldehyde to alcohol of from 10 to 1/1,000, production is typically carried out at a molar ratio within a range of from 1/2 to 1/50.

In the case of producing carboxylic acid ester from two types of alcohols as well, there are no particular limitations on the weight ratios of the types of alcohols, and production can be carried out at a molar ratio of one type of alcohol to another type of alcohol of from 10 to 1/1000 and preferably from 1/2 to 1/50.

Production of carboxylic acid ester can be carried out either in batches or continuously using any arbitrary method such as a vapor phase reaction, liquid phase reaction or irrigant reaction.

Although the reaction can be carried out in the absence of solvent, it can also be carried out using a solvent that is inert with respect to the reaction components, such as hexane, decane, benzene or dioxane.

Although the reaction can be carried out using a type of reaction known in the prior art, such as a fixed bed reaction, fluid bed reaction or stirred tank reaction, when carrying out the reaction in the liquid phase, for example, the reaction can be carried out using any type of reaction vessel, such as a bubble column reactor, draft tube reactor or stirred tank reactor.

The oxygen used in the production of carboxylic acid ester can be in the form of molecular oxygen, namely oxygen gas per se or a mixed gas in which oxygen gas is diluted with a diluent that is inert in the reaction, such as nitrogen or carbon dioxide gas, and air is preferably used for the oxygen raw material based on the ease of the procedure, economy and the like.

Although oxygen partial pressure varies according to the type of aldehyde, type of alcohol and other reaction materials, reaction conditions or type of reaction vessel and the like, in consideration of practical use, oxygen partial pressure at the reaction vessel outlet is within a range that is below the lower limit concentration of the explosive range thereof, and is preferably controlled to, for example, from 20 to 80 kPa. Although the reaction can be carried out over a wide range of arbitrary reaction pressures, from depressurization to pressurization, the reaction is generally carried out a pressure of from 0.05 to 2 MPa. It is preferable from the viewpoint of safety to set total pressure so that the oxygen concentration of the reaction vessel outflow gas does not exceed the explosion limit (oxygen concentration of, for example, 8%).

In the case of carrying out the carboxylic acid ester production reaction in a liquid phase and the like, the pH of the reaction system is preferably maintained at 6 to 9 by adding an alkaline metal or alkaline earth metal compound (such as an oxide, hydroxide, carbonate or carboxylate) to the reaction system. These alkaline metal or alkaline earth metal compounds can be used alone or two or more types can be used in combination.

Although production of carboxylic acid ester can be carried out at a high temperature of 200° C. and above for the reaction temperature, the reaction temperature is preferably from 30 to 200° C., more preferably from 40 to 150° C. and even more preferably from 60 to 120° C. There are no particular limitations on the reaction time, and although unable to be unconditionally defined since it varies according to the set conditions, is generally from 1 to 20 hours.

EXAMPLES

Although the following provides a more detailed explanation of the present embodiment through examples thereof, the present embodiment is not limited to these examples. A person with ordinary skill in the art is able to carry out the following examples as well as various variations thereof, and such variations are also included in the scope of claim for patent.

Furthermore, in the examples and comparative examples, determination of the loaded amounts of Ni and X and the atomic ratio of Ni/(Ni+X), determination of the contents of loaded constituent elements (Si, Al, basic metal, Mg), determination of the composition ratios of nickel and loaded constituent elements, analysis of nanoparticle crystal structure, analysis of the chemical state of catalyst metal components, morphological observation and elementary analysis of nanoparticles, measurement of the ultraviolet-visible spectra of the catalysts, analysis of the chemical state of nickel, measurement of support and catalyst physical properties (specific surface area, pore diameter, pore volume), observation of support and catalyst shape and measurement of average particle diameter were carried out according to the methods described below.

[Determination of Loaded Amounts of Ni and X and Atomic Ratio of Ni/(Ni+X)]

The concentrations of nickel and X in the catalyst were quantified using the IRIS Intrepid II Model XDL ICP Emission Analyzer (ICP-AES, MS) manufactured by Thermo Fisher Scientific K.K.

Samples were prepared by weighing out the catalyst into a Teflon decomposition vessel, adding sulfuric acid and hydrogen fluoride, decomposing by heating with the ETHOS TC microwave decomposition apparatus manufactured by Milestone General K.K.) and evaporating to dryness on a heater followed by adding nitric acid and hydrochloric acid to the precipitated residue, decomposing by heating with a microwave decomposition apparatus, and using a pure, fixed volume of the resulting decomposition liquid for the sample.

The quantification method was carried out by quantifying using the internal standard method by ICP-AES and subtracting the value of a simultaneously tested procedural blank to determine the contents of nickel and X in the catalyst and calculate the loaded amounts and atomic ratio.

[Determination of Contents of Loaded Constituent Elements (Si, Al, Basic Metal, Mg)]

Samples obtained by dissolving the support with sodium silicate, and samples obtained by dissolving with molten alkaline salt were prepared. The contents of basic metal and/or Mg were measured in the samples obtained by dissolving with sodium silicate, while the contents of Al and Si were measured in the samples dissolved with molten alkaline salt using the JY-38P2 ICP emission analyzer (ICP-AES) manufactured by Seiko Electronics Industry Co., Ltd., followed by calculation of the atomic ratios from the resulting metal contents.

[Determination of Composition Ratios of Nickel and Support Constituent Elements]

Atomic ratios were calculated from the contents of Ni, Al, Mg and basic metal as measured above.

[Analysis of Nanoparticle Crystal Structure]

Analysis of nanoparticle crystal structure was carried out using the Rint2500 Powder X-ray Diffraction System (XRD) manufactured by Rigaku Corp. under conditions of using a copper tube for the X-ray source (40 kV, 200 mA), measuring range of 5 to 65 degrees (0.02 deg/step), measuring speed of 0.2 deg/min and slit widths (scattering, divergence, reception) of 1 degree, 1 degree and 0.15 mm.

The catalyst samples were uniformly dispersed on a non-reflecting sample plate and fixed with a neoprene film.

[Analysis of Chemical State of Catalyst Metal Components]

Analysis of the chemical state of catalyst metal components was carried out using the ESCALAB 250 X-ray photoelectron spectroscopy (XPS) system manufactured by Thermo Electron Corp. under conditions of using Al Kα (15 kV×10 mA) for the excitation source, analyzed surface area of about 1 mm (shape: oval), using a survey scan (0 to 1, 100 eV) and narrow scan (Ni2p) for the uptake regions.

Measurement samples were prepared for XPS measurement by crushing catalyst particles with an agate mortar and pestle and sampling from a dedicated powder sample stand.

[Morphological Observation and Elementary Analysis of Nanoparticles]

TEM bright field images, STEM dark field images and STEM-EDS composition analyses (point analysis, mapping, line distribution) were measured using the Model 3100FEF transmission electron microscope/scanning transmission electron microscope (TEM/STEM) manufactured by JEOL (acceleration voltage: 300 kV, equipped with energy-dispersive X-ray detector (EDX)).

Data analysis software consisted of Digital Micrograph™ Ver. 1.70.16 (Gatan) for TEM and STEM analytical images (length measurement, Fourier transform analysis), and the NORAN System SIX Ver. 2.0 (Thermo Fisher Scientific) for EDS data analysis (mapping image processing, composition quantitative calculations).

Measurement samples were prepared by crushing catalyst particles with a mortar and pestle, dispersing in ethanol and subjecting to ultrasonic cleaning for about 1 minute followed by dropping onto a molybdenum (Mo) microgrid and exposing to air to obtain TEM/STEM observation samples.

[Measurement of Catalyst Ultraviolet-Visible Spectrum]

Measurement of catalyst UV-Vis spectrum was carried out using the Model V-550 ultraviolet-visible spectrophotometer (UV-Vis) manufactured by JASCO Corporation (integrating sphere unit, with powder sample holder) over a measuring range of 800 to 200 nm and at a scanning speed of 400 nm/min.

Measurement samples were prepared by crushing catalyst particles with a mortar and pestle, placing in the powder sample holder and applying to UV-Vis measurement.

[Analysis of Chemical State of Nickel]

Ni Kα spectra were measured with the Model XFRA-190 High-Resolution X-ray Fluorescence (HRXRF) manufactured by Technos Corp., and each of the resulting types of parameters were compared with those of standard substances (nickel metal, nickel oxide) to estimate the chemical state of nickel valence and the like in the catalysts.

The measurement samples were used for measurement without modification. Measurement of Ni Kα spectra was carried out in a partial spectral mode. At that time, a Ge (220) slit having a vertical angle of divergence of 1° was used for the analysis crystal, and excitation voltage and current were set to 35 kV and 80 mA, respectively. Filter paper was used for the absorber in the standard samples, counting time was selected for each sample in the catalyst samples, and measurements were carried out so that the peak intensity of the Kα spectrum was 3,000 cps or less and the counting time was 10,000 counts or more. Measurements were repeated five times on each sample, and a metal sample was measured before and after each repeated measurement. After performing smoothing processing (S-G method, 7 points, 5 cycles) on the measured spectra, the peak location, full width at half maximum (FWHM) and asymmetry coefficient (AI) were calculated, and the peak location was treated in the form of the displacement, or chemical shift ($\Delta E$), from the measured value of the metal sample measured before and after sample measurement.

[Support and Catalyst Physical Properties: Specific Surface Area, Pore Diameter, Pore Volume]

Measurements were carried out with the Autosoap 3MP manufactured by Yuasa Ionics Inc. using nitrogen for the adsorbent gas (nitrogen adsorption method). Specific surface area was measured using the BET method, pore diameter and pore size distribution were measured using the BJH method, and pore volume was measured by employing the adsorbed amount at the maximum $P/P_0$ ratio.

[Observation of Support and Catalyst Shape]

The support and catalyst particles were observed using the Model X-650 scanning electron microscope (SEM) manufactured by Hitachi, Ltd.

[Measurement of Support and Catalyst Average Particle Diameter]

Average particle diameter (volume-based) was measured using the Model LS230 Laser Diffraction Particle Size Analyzer manufactured by Beckman-Coulter, Inc.

Reference Example 1

Using 0.5 g of commercially available nickel oxide (Wako Pure Chemical Industries, Ltd.) as catalyst, 1.0 g of methacrolein and 10 mL of methanol were charged into a high-pressure autoclave-type reaction vessel (total volume: 120 mL) made of SUS316 provided with a magnetic stirrer. After closing the autoclave and replacing the inside of the system with a nitrogen gas, a nitrogen mixed gas containing 7 vol % of oxygen was introduced into a vapor phase unit and the total pressure inside the system was increased to 3.0 MPa. Next, the reaction vessel was immobilized in an oil bath and the reaction was carried out for 2 hours at a reaction temperature of 80° C. while stirring. After cooling, residual pressure was released and the autoclave was opened followed by filtering out the catalyst and analyzing the filtrate by gas chromatography. As a result, the amount of methyl methacrylate formed was 1.0 µmol.

Reference Example 2

A reaction was carried out in the same manner as Reference Example 1 with the exception of using nickel peroxide hydrate (Aldrich Corp.) for the catalyst instead of nickel oxide. As a result, the amount of methyl methacrylate formed was 5.3 µmol.

Reference Example 3

A reaction was carried out in the same manner as Reference Example 1 with the exception of using nickel metal (Wako Pure Chemical Industries, Ltd.) for the catalyst instead of nickel oxide. As a result, the formation of methyl methacrylate was unable to be confirmed.

Example 1

(1) Catalyst Preparation 30 g of commercially available γ-alumina (Neobead, Mizusawa Industrial Chemicals, Ltd.) were added to a glass container containing 100 mL of distilled water followed by dropping in prescribed amounts of an aqueous nickel nitrate solution and aqueous palladium chloride solution while stirring at 60° C., adding 0.5 N aqueous sodium hydroxide solution to adjust the pH of the aqueous solutions to 8, continuing to stir for 1 hour, allowing to stand undisturbed, removing the supernatant, washing with distilled water until Cl ion was no longer detected, drying for 16 hours at 105° C. and firing in air for 5 hours at 600° C. Next, the resulting catalyst was subjected to reducing treatment for 1 hour at room temperature under a hydrogen atmosphere to obtain a catalyst loaded with 1.5% by mass of nickel and 0.5% by mass of palladium (NiOPd/γ-alumina). The atomic ratio of Ni/(Ni+Pd) of the resulting catalyst was 0.84. Based on the results of X-ray diffraction (XRD), diffraction patterns attributable to nickel were not observed, thus confirming nickel to be present in an amorphous state. On the other hand, although not able to be defined as a well-defined peak, a broad peak was present corresponding to palladium crystals. Although the value of this peak was close to the powder X-ray diffraction detection limit (2 nm), calculation of the average crystallite size using Scherrer's formula yielded a value of about 3 nm. With respect to the chemical state of the Ni, the valence was confirmed to be 2 based on the results of X-ray photoelectron spectroscopy (XPS).

In addition, observation of the form of the active species of the catalyst with a transmission electron microscope (TEM/STEM) confirmed that nanoparticles having a maximum particle diameter distribution of from 3 to 4 nm (number average particle diameter: 3.8 nm) were loaded on the support. An elementary analysis (20 points) was carried out on each observed nanoparticle by ancillary energy-dispersive X-ray spectroscopy (EDX), and nickel and palladium were confirmed in all of the particles. The atomic ratio of nickel to palladium of these composite particles (mean value) was 1.24.

(2) Synthesis of Carboxylic Acid Ester 0.2 g of the catalyst obtained in (1) above, 1.0 g of methacrolein and 10 mL of methanol were charged into a high-pressure autoclave-type reaction vessel (total volume: 120 mL) made of SUS316 and provided with a magnetic stirrer. After closing the autoclave and replacing the inside of the system with nitrogen, a mixed nitrogen gas containing 7 vol % oxygen was introduced into a vapor phase unit and the pressure inside the system was increased to 3.0 MPa.

Next, the reaction vessel was immobilized in an oil bath and a reaction was carried out for 1 hour at a reaction temperature of 80° C. while stirring. After cooling, residual pressure was released and the autoclave was opened followed by filtering out the catalyst and analyzing the filtrate by gas chromatography. As a result, the methacrolein conversion rate was 18.2% and methyl methacrylate selectivity was 74.5%.

Example 2

A catalyst was prepared in the same manner as in (1) of Example 1 with the exception of using an aqueous silver nitrate solution instead of an aqueous palladium chloride solution. The loaded amounts of nickel and silver of the resulting catalyst were 1.6% by mass and 1.3% by mass, respectively (NiOAg/γ-alumina). In addition, the atomic ratio of Ni/(Ni+Ag) was 0.69. Based on the results of powder X-ray diffraction (XRD), a broad peak was present corresponding to silver crystals. Calculation of the average crystallite size thereof according to Scherrer's formula yielded a value of about 4 nm. On the other hand, a diffraction pattern attributable to nickel was not observed, thus confirming that nickel is present in an amorphous state. With respect to the chemical state of Ni, the valence was confirmed to be 2 based on the results of X-ray photoelectron spectroscopy (XPS).

Observation of the form of the active species of the catalyst with a transmission electron microscope (TEM/STEM) confirmed that nanoparticles having a maximum particle diameter distribution of 4 to 5 nm (number average particle diameter: 4.2 nm) were loaded on the support. An elementary analysis (20 points) was carried out on each observed nanoparticle by ancillary energy-dispersive X-ray spectroscopy (EDX), and nickel and silver were confirmed in all of the particles. The atomic ratio of nickel to silver of these composite particles (mean value) was 0.81.

In addition, as a result of investigating changes in the electron excitation state of this catalyst by ultraviolet-visible spectroscopy (UV-Vis), surface plasmon absorption peaks originating from silver nanoparticles were not observed in the vicinity of 405 nm, while broad absorbance attributable to $NiO_2$ was observed over a wavelength range from 200 to 800 nm.

A reaction was carried out in the same manner as (2) of Example 1 using this catalyst. As a result, the methacrolein conversion rate was 6.2% and methyl methacrylate selectivity was 55.1%.

Example 3

A catalyst was prepared in the same manner as in (1) of Example 1 with the exception of using an aqueous chloroauric acid solution instead of an aqueous palladium chloride solution. The loaded amounts of nickel and gold of the resulting catalyst were 1.4% by mass and 0.4% by mass, respectively (NiOAu/γ-alumina). In addition, the atomic ratio of Ni/(Ni+Au) was 0.92. Based on the results of powder X-ray diffraction (XRD), a diffraction pattern attributable to nickel was not observed, thus confirming that nickel is present in an amorphous state. On the other hand, although not able to be defined as a well-defined peak, a broad peak was present corresponding to gold crystals. Although the value of this peak was close to the powder X-ray diffraction detection limit (2 nm), calculation of the average crystallite size using Scherrer's formula yielded a value of about 3 nm. With respect to the chemical state of the Ni, the valence was confirmed to be 2 based on the results of X-ray photoelectron spectroscopy (XPS).

Observation of the form of the active species of the catalyst with a transmission electron microscope (TEM/STEM) confirmed that nanoparticles having a maximum particle diameter distribution of from 2 to 3 nm (number average particle diameter: 3.2 nm) were loaded on the support. An elementary analysis (20 points) was carried out on each observed nanoparticle by ancillary energy-dispersive X-ray spectroscopy (EDX), and nickel and gold were confirmed in all of the particles. The atomic ratio of nickel to gold of these composite particles (mean value) was 1.14.

As a result of investigating changes in the electron excitation state of this catalyst by ultraviolet-visible spectroscopy (UV-Vis), surface plasmon absorption peaks originating from gold nanoparticles were not observed in the vicinity of 530 nm, while broad absorbance attributable to $NiO_2$ was observed over a wavelength range from 200 to 800 nm.

A reaction was carried out in the same manner as (2) of Example 1 using this catalyst. As a result, the methacrolein conversion rate was 22.4% and methyl methacrylate selectivity was 92.4%.

Reference Example 4

A catalyst loaded with 1.5% by mass nickel (NiO/γ-alumina) was obtained by preparing a catalyst in the same manner as (1) of Example 1 with the exception of not adding an aqueous palladium chloride solution and not carrying out hydrogen reduction.

A reaction was carried out in the same manner as (2) of Example 1 using this catalyst. As a result, the conversion rate of methacrolein was 3.1% and methyl methacrylate selectivity was 35.2%.

Comparative Example 1

A catalyst loaded with 0.5% by mass of palladium (Pd/γ-alumina) was obtained by preparing a catalyst in the same manner as (1) of Example 1 with the exception of not adding nickel nitrate. Based on the results of powder X-ray diffraction (XRD), a broad peak was present corresponding to palladium crystals. Calculation of the average crystallite size thereof according to Scherrer's formula yielded a value of about 3 nm.

A reaction was carried out in the same manner as in (2) of Example 1 using this catalyst. As a result, the conversion rate of methacrolein was 10.3% and methyl methacrylate selectivity was 52.4%.

Comparative Example 2

A catalyst loaded with 1.5% by mass of silver (Ag/γ-alumina) was obtained by preparing a catalyst in the same manner as (1) of Example 1 with the exception of using aqueous silver nitrate solution instead of aqueous palladium chloride solution and not adding nickel nitrate. Based on the results of powder X-ray diffraction (XRD), a broad peak was present corresponding to silver crystals. Calculation of the average crystallite size thereof according to Scherrer's formula yielded a value of about 5 nm. As a result of investigating changes in the electron excitation state of this catalyst by ultraviolet-visible spectroscopy (UV-Vis), surface plasmon absorption peaks originating from silver nanoparticles were observed in the vicinity of 405 nm.

A reaction was carried out in the same manner as in (2) of Example 1 using this catalyst. As a result, the conversion rate of methacrolein was 2.1% and methyl methacrylate selectivity was 25.3%.

Comparative Example 3

A catalyst loaded with 1.5% by mass of nickel and 1.4% by mass of silver (NiAg/γ-alumina) was obtained by preparing a catalyst in the same manner as (1) of Example 1 with the exception of using an aqueous silver nitrate solution instead of an aqueous palladium chloride solution and changing the heat treatment atmosphere from air to hydrogen.

Based on the results of powder X-ray diffraction (XRD) and X-ray photoelectron spectroscopy (XPS), nickel was confirmed to have been reduced to a metal state, and an alloy of nickel and silver was confirmed to have been formed.

A reaction was carried out in the same manner as in (2) of Example 1 using this catalyst. As a result, the conversion rate of methacrolein was 1.5% and methyl methacrylate selectivity was 5.1%.

Table 1 shows the physical properties and reaction results for the catalysts for production of carboxylic acid ester of Examples 1 to 3, Reference Example 4 and Comparative Examples 1 to 3.

TABLE 1

| No. | Loaded Composite Nanoparticles | Ni and X Loaded Amounts (% by mass) | | Ni/(Ni + X) Atomic Ratio (mol %) | Reaction Results | |
|---|---|---|---|---|---|---|
| | | Ni | X | | Conversion Rate (%) | MMA Selectivity (%) |
| Example 1 | NiOPd/Al$_2$O$_3$ | 1.5 | 0.5 | 0.84 | 18.2 | 74.5 |
| Example 2 | NiOAg/Al$_2$O$_3$ | 1.6 | 1.3 | 0.69 | 6.2 | 55.1 |
| Example 3 | NiOAu/Al$_2$O$_3$ | 1.4 | 0.4 | 0.92 | 22.4 | 92.4 |
| Reference Example 4 | NiO/Al$_2$O$_3$ | 1.5 | 0 | — | 3.1 | 35.2 |
| Comparative Example 1 | Pd/Al$_2$O$_3$ | 0 | 0.5 | — | 10.3 | 52.4 |
| Comparative Example 2 | Ag/Al$_2$O$_3$ | 0 | 1.5 | — | 2.1 | 25.3 |
| Comparative Example 3 | NiAg/Al$_2$O$_3$ | 1.5 | 1.4 | — | 1.5 | 5.1 |

Example 4

A magnesium compound was impregnated and loaded onto commercially available silica (CARiACT Q-15, Fuji Silysia Chemical, Ltd.) over a hot water bath using an aqueous solution containing magnesium acetate. Next, the resulting impregnated product was dried for 12 hours at 120° C. followed by firing in air for 6 hours at 600° C. As a result, a silica-magnesia support (SiO$_2$—MgO) was obtained that contained 5% by mass of magnesium oxide as Mg.

Next, 100 mL of an aqueous solution containing prescribed amounts of an aqueous nickel nitrate solution and an aqueous chloroauric acid solution was heated at 80° C. 30 g of the silica-magnesia support obtained above was added to this solution followed by stirring for one hour while holding this mixture under stirring, thereby precipitating nickel and gold components onto the support. Next, this mixture was allowed to stand undisturbed and the supernatant was removed followed by washing with distilled water until Cl ions were no longer detected. After that, this mixture was filtered and dried for 16 hours at 105° C. and firing for 3 hours in air at 500° C. to obtain a catalyst loaded with 1.0% by mass of nickel and 0.8% by mass of gold (NiOAu/SiO$_2$—MgO). The atomic ratio of Ni/(Ni+Au) of the resulting catalyst was 0.81.

According to the results of powder X-ray diffraction (XRD) of the catalyst described above, a broad diffraction peak attributable to gold was observed, and calculation of average crystallite size based on the spread of the line width of the diffraction peak attributable to the Au (111) surface yielded a value of 3 nm. On the other hand, since there were no diffraction patterns originating from nickel, the nickel was presumed to be present in an amorphous phase. With respect to the chemical state of the nickel, the valence was confirmed to be 2 based on the results of X-ray photoelectron spectroscopy (XPS).

Figure 2:
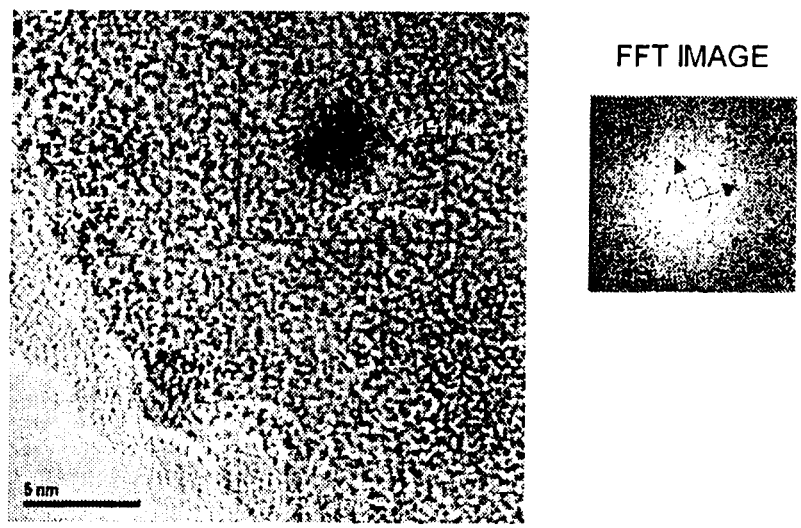
FIG. 2 shows an enlarged photomicrograph of FIG. 1 and an image thereof obtained by fast Fourier transformation (FFT)

The microstructure of the above catalyst was observed using a transmission electron microscope (TEM/STEM). As shown in FIG. 1, spherical particles having a particle diameter of from 2 to 3 nm are uniformly loaded on the support surface. The number average particle diameter of the nanoparticles was 3.0 nm (number of nanoparticles used for calculation: 100). The nanoparticles were observed to have a lattice pattern in further enlarged images of the nanoparticles (FIG. 2). As a result of analyzing by Fourier transformation, a lattice pattern corresponding to the lattice spacing of Au (200) (d=2.039 Å) intersected at 90° C., thus indicating this to be the lattice image of Au (200). Thus, the nanoparticles comprised crystalline gold. Lattice patterns corresponding to the lattice spacing of Au (200) and Au (111) were also observed in other particles.

Figure 3:
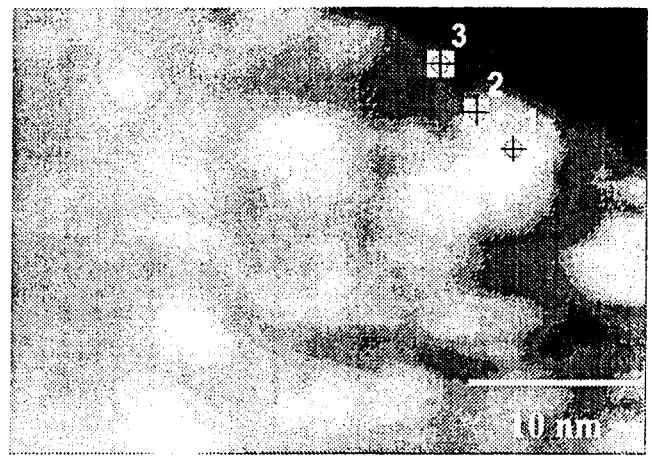
FIG. 3 shows a photomicrograph obtained with a scanning transmission electron microscope (STEM bright field image) of the catalyst for producing carboxylic acid ester of Example 4 along with the results of an analysis of composition points by energy dispersive X-ray spectroscopy.
Figure 4:
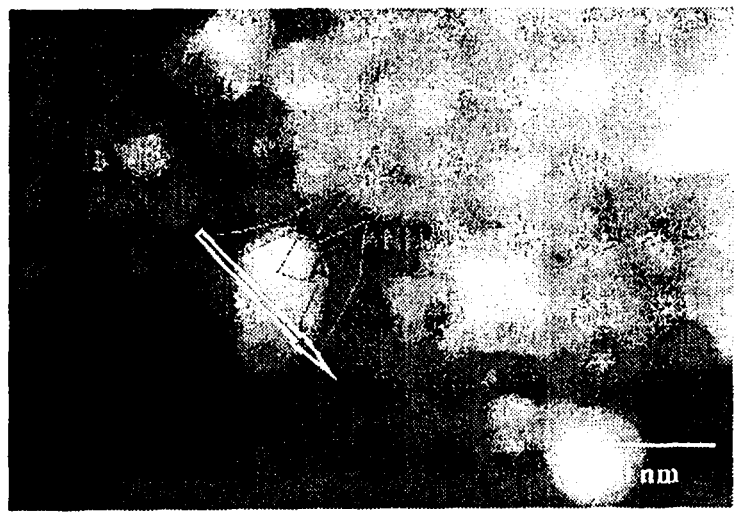
FIG. 4 shows photomicrographs obtained with the scanning transmission electron microscope (STEM bright field image) of the catalyst for producing carboxylic acid ester of Example 4 along with the results of a line profile of the composition thereof obtained by energy dispersive X-ray spectroscopy.
Figure 4:
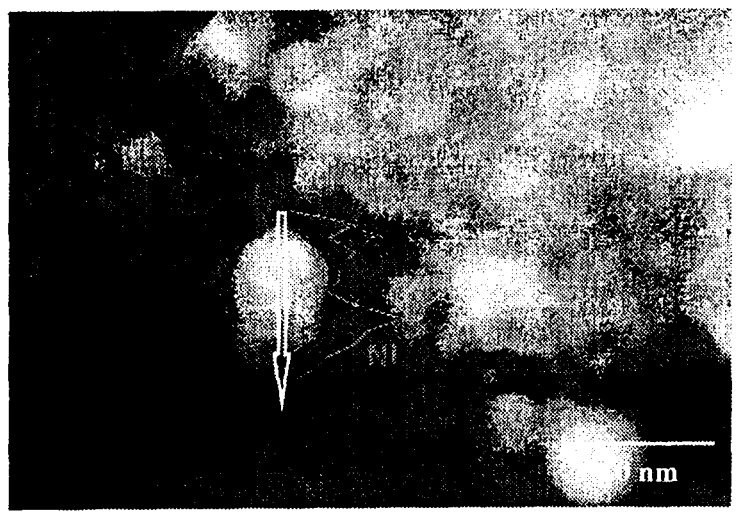

Next, analysis of composition points by STEM-EDS for each nanoparticle indicated that nickel and gold were detected in each particle. The mean value of the ratio of nickel/gold atoms of the nanoparticles (number of nanoparticles used for calculation: 50) was 0.82. Only trace amounts of nickel were detected at analysis points other than the nanoparticles. Moreover, when nanoregions of the observed particles were analyzed (FIG. 3), the atomic ratio of Ni/Au at the centers of the particles (measurement point 1) was 0.73, while that at the particle edge (measurement point 2) was 2.95. Only trace amounts of nickel were detected at other portions of the particles (measurement point 3). As a result of carrying out similar measurements 20 times, larger amounts of nickel were detected around the edges of all particles. The distribution of nickel and gold was observed to nearly completely agree with this based on the results of EDS element mapping. In addition, nickel was distributed one circumference larger than the distribution of gold in all scanning directions (1, 2) based on composition line profiles (FIG. 4). In this manner, since nickel is distributed over the gold and nickel is detected in larger amounts around the edges of the particles, the nanoparticles contained in the above-mentioned catalyst are considered to have a form in which the surfaces of gold nanoparticles are covered with nickel.

Figure 5:
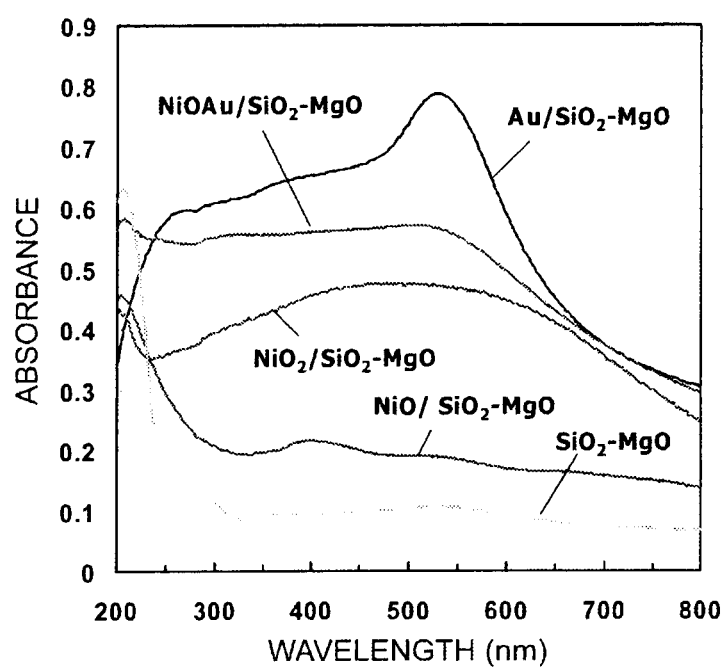
FIG. 5 shows a graph showing analyses by ultraviolet-visible spectroscopy of the catalyst for producing carboxylic acid ester of Example 4.

FIG. 5 shows the absorption spectra of NiOAu/SiO$_2$—MgO catalyst particles using ultraviolet-visible spectroscopy (UV-Vis). The Au/SiO$_2$—MgO sample has gold nanoparticles loaded on the same support (catalyst prepared in Comparative Example 4 to be described later), and surface plasmon absorption originating from the gold nanoparticles appears in the vicinity of 530 nm. The MO/SiO$_2$—MgO sample (catalyst prepared in Reference Example 5 to be described later) and NiO$_2$/SiO$_2$—MgO sample (synthesized by subjecting the sample prepared in Reference Example 5 to oxidizing treatment with hypochlorous acid) have fine particles of NiO and NiO$_2$ loaded on the same support, and broad absorbance over a wavelength range of 200 to 800 nm observed with NiO$_2$/SiO$_2$—MgO was no longer observed with MO/SiO$_2$—MgO. This result means that broad absorbance over the wavelength range of 200 to 800 nm is demonstrated in case of highly oxidized nickel oxide (NiO$_2$). In contrast, surface plasmon absorption of gold in the vicinity of 530 nm does not appear in the case of NiOAu/SiO$_2$—MgO, and broad absorbance attributable to NiO$_2$ is observed over the wavelength range of 200 to 800 nm.

On the basis of these results, NiOAu/SiO$_2$—MgO catalysts are believed to be of a form in which gold atoms are not present on the surface thereof, but rather the surfaces of gold nanoparticles are covered with highly oxidized nickel oxide.

0.3 g of the catalyst obtained above, 1.0 g of methacrolein and 10 mL of methanol were charged into a high-pressure autoclave-type reaction vessel (total volume: 120 mL) made of SUS316 and provided with a magnetic stirrer, and after closing the autoclave and replacing the inside of the system with nitrogen gas, a nitrogen mixed gas containing 7 vol % oxygen was introduced into a vapor phase unit followed by increasing the pressure inside the system to 5.0 MPa.

Next, the reaction vessel was immobilized in an oil bath and a reaction was carried out for 2 hours at a reaction temperature of 60° C. while stirring. After cooling, residual pressure was released and the autoclave was opened followed by filtering out the catalyst and analyzing the filtrate by gas chromatography.

As a result, the conversion rate of methacrolein was 61.3% and methyl methacrylate selectivity was 95.7%.

Reference Example 5

A catalyst loaded with 1.0% by mass of nickel (Ni/SiO$_2$—MgO) was obtained by preparing in the same manner as Example 4 with the exception of not adding aqueous chloroauric acid solution.

A reaction was carried out in the same manner as Example 4 using this catalyst. As a result, the methacrolein conversion rate was 3.2% and methyl methacrylate selectivity was 30.1%.

Comparative Example 4

A catalyst loaded with 0.9% by mass of gold (Au/SiO$_2$—MgO) was obtained by preparing in the same manner as Example 4 with the exception of not adding nickel nitrate. The average crystallite size as calculated by powder X-ray diffraction (XRD) was 3 nm.

A reaction was carried out in the same manner as Example 4 using this catalyst. As a result, the methacrolein conversion rate was 9.7% and methyl methacrylate selectivity was 75.0%.

Comparative Example 5

A catalyst loaded with 1.0% by mass of nickel and 0.8% by mass of gold (NiAu/SiO$_2$—MgO) was obtained by preparing in the same manner as Example 4 with the exception of changing the heat treatment atmosphere from air to hydrogen. Based on the results of X-ray diffraction (XRD) and X-ray photoelectron spectroscopy (XPS) of this catalyst, the nickel was reduced to a metal state, and an alloy of nickel and gold was confirmed to have been formed.

A reaction was carried out in the same manner as Example 4 using this catalyst. As a result, the methacrolein conversion rate was 11.3% and methyl methacrylate selectivity was 62.4%.

Comparative Example 6

A catalyst loaded with 1.1% by mass of iron and 0.9% by mass of gold (Fe$_2$O$_3$Au/SiO$_2$—MgO) was obtained by preparing in the same manner as Example 4 with the exception of using iron nitrate instead of nickel nitrate. The atomic ratio of Fe/(Fe+Au) of the resulting catalyst was 0.81.

Based on the results of measuring the ultraviolet-visible (UV-Vis) spectrum of this catalyst, surface plasmon absorption originating from gold nanoparticles (at about 530 nm) was observed.

A reaction was carried out in the same manner as Example 4 using this catalyst. As a result, the methacrolein conversion rate was 10.4% and methyl methacrylate selectivity was 55.2%.

Comparative Example 7

A catalyst loaded with 1.2% by mass of cobalt and 0.8% by mass of gold (Co$_3$O$_4$Au/SiO$_2$—MgO) was obtained by preparing in the same manner as Example 4 with the exception of using cobalt nitrate instead of nickel nitrate. The atomic ratio of Co/(Co+Au) of the resulting catalyst was 0.83.

Based on the results of measuring the ultraviolet-visible (UV-Vis) spectrum of this catalyst, surface plasmon absorption originating from gold nanoparticles (at about 530 nm) was observed.

A reaction was carried out in the same manner as Example 4 using this catalyst. As a result, the methacrolein conversion rate was 2.6% and methyl methacrylate selectivity was 45.8%.

Comparative Example 8

A catalyst loaded with 1.0% by mass of copper and 0.8% by mass of gold (CuOAu/SiO$_2$—MgO) was obtained by preparing in the same manner as Example 4 with the exception of using copper nitrate instead of nickel nitrate. The atomic ratio of Cu/(Cu+Au) of the resulting catalyst was 0.79.

Based on the results of measuring the ultraviolet-visible (UV-Vis) spectrum of this catalyst, surface plasmon absorption originating from gold nanoparticles (at about 530 nm) was observed.

A reaction was carried out in the same manner as Example 4 using this catalyst. As a result, the methacrolein conversion rate was 9.2% and methyl methacrylate selectivity was 58.1%.

Table 2 shows the physical properties and reaction results for the catalysts for production of carboxylic acid ester of Example 4, Reference Example 5 and Comparative Examples 4 to 8.

TABLE 2

| No. | Loaded Composite Nanoparticles | Ni and Au Loaded Amounts (% by mass) | | Ni/(Ni + Au) Atomic Ratio (mol %) | Reaction Results | |
|---|---|---|---|---|---|---|
| | | Ni | Au | | Conversion Rate (%) | MMA Selectivity (%) |
| Example 4 | NiOAu/SiO$_2$—MgO | 1.0 | 0.8 | 0.81 | 61.3 | 95.7 |
| Reference Example 5 | NiO/SiO$_2$—MgO | 1.0 | 0 | 1.00 | 3.2 | 30.1 |
| Comparative Example 4 | Au/SiO$_2$—MgO | 0 | 0.9 | — | 9.7 | 75.0 |
| Comparative Example 5 | NiAu/SiO$_2$—MgO | 1.0 | 0.8 | 0.81 | 11.3 | 62.4 |
| Comparative Example 6 | Fe$_2$O$_3$Au/SiO$_2$—MgO | 1.1[1)] | 0.9 | 0.81[4)] | 10.4 | 55.2 |
| Comparative Example 7 | Co$_3$O$_4$Au/SiO$_2$—MgO | 1.2[2)] | 0.8 | 0.83[5)] | 2.6 | 45.8 |
| Comparative Example 8 | CuOAu/SiO$_2$—MgO | 1.0[3)] | 0.8 | 0.79[6)] | 9.2 | 58.1 |

[1)]loaded amount of Fe,
[2)]loaded amount of Co,
[3)]loaded amount of Cu,
[4)]atomic ratio of Fe/(Fe + Au),
[5)]atomic ratio of Co/(Co + Au),
[6)]atomic ratio of Cu/(Cu + Au)

Examples 5 to 10, Reference Example 6, Comparative Example 9

2 kg of silica sol (Snowtex N-30 manufactured by Nissan Chemical Industries, Ltd. (SiO$_2$ content: 30% by mass)) were added to 128 g of titania sol (STS-018 manufactured by Ishihara Techno Co., Ltd. (TiO$_2$ content: 30% by mass)) and mixed followed by holding the slurry for 24 hours at 15° C. and spray drying with a spray dryer set to an outlet gas temperature of 130° C. to obtain a solid.

Next, a silica-titania support was obtained by firing for 2 hours in air at 300° C. and then for 3 hours at 600° C. The silica/titania ratio as oxides was 93.6/6.0. Specific surface area as determined by the nitrogen adsorption method was 236 m$^2$/g, and pore volume was 0.26 mL/g. The average particle diameter of the support was 60 μm based on results obtained with a laser diffraction particle size analyzer. In addition, the shape of the support was determined to be nearly spherical based on observations made using a scanning electron microscope (SEM).

Next, 30 g of the silica-titania support obtained above were added to a glass container containing 100 mL of distilled water, followed, while being stirred at 90° C., by dropping in prescribed amounts of an aqueous nickel nitrate solution and aqueous chloroauric acid solution, adjusting the pH of the aqueous solution to 7 by adding 0.5 N aqueous sodium hydroxide solution and continuing to stir for 1 hour. Subsequently, the aqueous solution was allowed to stand undisturbed and the supernatant was removed followed by washing with distilled water until Cl ions were no longer detected, drying for 16 hours at 105° C. and firing for 3 hours at 400° C. in air to prepare a catalyst in which the atomic ratio of Ni/(Ni+Au) was changed to within a range of from 0 to 1.0 (while the total amount of nickel and gold remained constant), after which a reaction was carried out in the same manner as Example 4. Table 3 shows the physical properties of the resulting catalysts along with formation activity for methyl methacrylate per unit molar amounts of nickel and gold (MMA mol/h/mol-Ni+Au).

TABLE 3

| No. | Loaded Composite Nanoparticles | Ni and Au Loaded Amounts (% by mass) | | Ni/(Ni + Au) Atomic Ratio (mol %) | MMA Formation Activity (MMA mol/h/ mol-Ni + Au) |
|---|---|---|---|---|---|
| | | Ni | Au | | |
| Example 5 | NiOAu/SiO$_2$—TiO$_2$ | 1.2 | 0.4 | 0.91 | 25.2 |
| Example 6 | NiOAu/SiO$_2$—TiO$_2$ | 1.1 | 0.7 | 0.83 | 41.3 |
| Example 7 | NiOAu/SiO$_2$—TiO$_2$ | 0.9 | 1.3 | 0.70 | 63.5 |
| Example 8 | NiOAu/SiO$_2$—TiO$_2$ | 0.8 | 1.7 | 0.61 | 52.1 |
| Example 9 | NiOAu/SiO$_2$—TiO$_2$ | 0.7 | 2.1 | 0.53 | 43.7 |
| Example 10 | NiOAu/SiO$_2$—TiO$_2$ | 0.3 | 3.5 | 0.22 | 14.0 |
| Reference Example 6 | NiO/SiO$_2$—TiO$_2$ | 1.3 | 0 | 1.00 | 0.4 |
| Comparative Example 9 | Au/SiO$_2$—TiO$_2$ | 0 | 4.3 | 0 | 8.3 |

Example 11

A methyl acrylate formation reaction was carried out using the same procedure and reaction conditions as Example 4 with the exception of using the catalyst prepared in Example 4 (NiOAu/SiO$_2$—MgO) and reacting acrolein instead of methacrolein.

As a result, the acrolein conversion rate was 71.3% and methyl acrylate selectivity was 96.8%.

Example 12

An ethyl acrylate formation reaction was carried out using the same procedure and reaction conditions as Example 4 with the exception of using the catalyst prepared in Example 4 (NiOAu/SiO$_2$—MgO), reacting acrolein instead of methacrolein, and reacting ethanol instead of methanol.

As a result, the acrolein conversion rate was 81.5% and ethyl acrylate selectivity was 96.2%.

Example 13

An ethyl benzoate formation reaction was carried out using the same procedure and reaction conditions as Example 4 with the exception of using the catalyst prepared in Example 4 (NiOAu/SiO$_2$—MgO), reacting benzaldehyde instead of methacrolein, and reacting ethanol instead of methanol.

As a result, the benzaldehyde conversion rate was 88.2% and ethyl benzoate selectivity was 98.2%.

Example 14

A methyl methacrylate formation reaction was carried out using the same procedure and reaction conditions as Example 4 with the exception of using the catalyst prepared in Example 4 (NiOAu/SiO$_2$—MgO) and reacting methallyl alcohol instead of methacrolein.

As a result, the methallyl alcohol conversion rate was 59.2% and methyl acrylate selectivity was 94.1%.

Example 15

An ethyl acetate formation reaction was carried out using the same procedure and reaction conditions as Example 4 with the exception of using the catalyst prepared in Example 4 (NiOAu/SiO$_2$—MgO), reacting ethanol instead of methacrolein and methanol and making the reaction temperature 80° C.

As a result, the ethanol conversion rate was 30.4% and ethyl acetate selectivity was 91.2%.

Example 16

A methyl glycolate formation reaction was carried out using the same procedure and reaction conditions as Example 4 with the exception of using the catalyst prepared in Example 4 (NiOAu/SiO$_2$—MgO) and reacting ethylene glycol instead of methacrolein.

As a result, the ethylene glycol conversion rate was 42.4% and methyl glycolate selectivity was 90.5%.

Example 17

(1) Support Preparation

An aqueous solution in which 4.16 kg of aluminum nitrate nonahydrate and 540 g of 60% nitric acid were dissolved in 5.0 L of pure water was gradually dropped into 20.0 kg of a stirred silica sol solution having a colloidal particle diameter of from 10 to 20 nm held at 15° C. (Snowtex N-30 manufactured by Nissan Chemical Industries, Ltd. (SiO$_2$ content: 30% by mass)) to obtain a mixed slurry of silica sol and aluminum nitrate. Subsequently, the mixed slurry was aged by holding at 50° C. for 24 hours. After cooling to room temperature, the mixed slurry was spray-dried with a spray dryer set to an outlet temperature of 130° C. to obtain a solid.

Next, the resulting solid was filled to a thickness of about 1 cm into a stainless steel container with the top being open followed by heating in an electric oven from room temperature to 300° C. over the course of 2 hours and then holding at that temperature for 3 hours. After further heating to 600° C. over the course of 2 hours followed by holding at that temperature for 3 hours, the solid was cooled gradually to obtain a silica-alumna support. The amount of aluminum in the resulting support was 10 mol % based on the total molar amount of silicon and aluminum. Specific surface area as determined according to the nitrogen adsorption method was 145 m$^2$/g, pore volume was 0.27 mL/g, and average pore diameter was 8 nm. The average particle diameter of the support based on the results of measuring with a laser diffraction particle size analyzer was 62 µm. In addition, the shape of the support was found to be nearly spherical based on observations with a scanning electron microscope (SEM).

(2) Catalyst Production 1.0 L of a solution containing 22.30 g of nickel nitrate hexahydrate and 20 mL of a 1.3 mol/L aqueous chloroauric acid solution was heated to 80° C. 300 g of the silica-alumina support obtained above were placed in this aqueous solution followed by adjusting the pH of the aqueous solution to 7 by addition of 0.5 N aqueous sodium hydroxide solution while holding at 80° C. and stirring and continuing to stir for 1 hour to deposit the nickel and gold components onto the support.

Next, after allowing to stand undisturbed, removing the supernatant and washing several times with distilled water, the liquid was filtered. After drying the filtrate for 16 hours at 105° C., the product was fired for 5 hours at 450° C. in air to obtain a catalyst loaded with 1.43% by mass of nickel and 1.45% by mass of gold (NiOAu/SiO$_2$—Al$_2$O$_3$). The atomic ratio of Ni/(Ni+Au) of the resulting catalyst was 0.768, and the atomic ratio of Ni/Al was 0.144. Specific surface area as determined by the nitrogen adsorption method was 150 m$^2$/g, pore volume was 0.28 mL/g, and average pore diameter was 8 nm. The average particle diameter of the catalyst based on the results of measuring with a laser diffraction particle size analyzer was 61 µm. In addition, the shape of the catalyst was found to be nearly spherical based on observations with a scanning electron microscope (SEM).

Based on the results of powder X-ray diffraction (XRD), a diffraction pattern originating from nickel was not observed, and the nickel was confirmed to be present in an amorphous state. On the other hand, although not able to be defined as a well-defined peak, a broad peak was present corresponding to gold crystals. Although the value of this peak was close to the powder X-ray diffraction detection limit (2 nm), calculation of the average crystallite size using Scherrer's formula yielded a value of about 3 nm.

With respect to the chemical state of the Ni, the valence was confirmed to be 2 based on the results of X-ray photoelectron spectroscopy (XPS). Moreover, the chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.458 and the chemical shift (ΔE) was 0.331. The full width at half maximum (FWHM) of the Ni Kαspectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.2 nm) were loaded on the support. Observation of enlarged images of the nanoparticles demonstrated that the nanoparticles had a lattice pattern corresponding to the lattice spacing of Au (111). Analysis of composition points by STEM-EDS for each nanoparticle confirmed that nickel and gold were contained in each particle. The mean value of the ratio of nickel/gold atoms of the composite nanoparticles (number of nanoparticles used for calculation: 50) was 0.83. Moreover, when nanoregions of the observed particles were analyzed, nickel was distributed over the gold in all particles, and larger amounts of nickel were detected around the particle edges.

Next, as a result of investigating changes in the electron excitation state of this catalyst by ultraviolet-visible spectroscopy (UV-Vis), surface plasmon absorption peaks originating from gold nanoparticles were not observed in the vicinity of 530 nm, while broad absorbance attributable to $NiO_2$ was observed over a wavelength range from 200 to 800 nm.

On the basis of these results, nanoparticles contained in the catalyst according to the present embodiment were confirmed to have a form in which the surface of gold nanoparticles is covered with nickel, and have a different surface electron state than that of gold nanoparticles comprised of a single metal species.

(3) Synthesis of Carboxylic Acid Ester 200 g of the catalyst obtained above (NiOAu/$SiO_2$—$Al_2O_3$) were charged into a stirring reaction vessel made of stainless steel having a liquid phase unit of 1.2 liters and provided with a catalyst separator. An oxidative carboxylic acid ester formation reaction was then carried out using aldehyde and alcohol or one or more types of alcohols while stirring the contents of the reaction vessel at a stirrer tip speed of 4 m/s. A 36.7% by mass of methacrolein/methanol solution was continuously supplied to the reaction vessel at the rate of 0.6 liters/hr, while a 1 to 4% by mass of NaOH/methanol solution was continuously supplied at the rate of 0.06 liters/hr, air was blown in such that the reaction temperature was 80° C. and the outlet oxygen concentration at a reaction pressure of 0.5 MPa was 4.0 vol % (equivalent to oxygen partial pressure of 0.02 MPa), and the concentration of NaOH supplied to the reaction vessel was controlled so that the pH of the reaction system was 7. The reaction product was continuously extracted from the reaction vessel outlet by overflow, and the reactivity was investigated by analyzing by gas chromatography.

After 200 hours from the start of the reaction, the methacrolein conversion rate was 61.5%, methyl methacrylate selectivity was 94.6%, and methyl methacrylate formation activity per catalyst unit weight was 7.60 mol/h/kg-cat. Reactivity after 500 hours had elapsed did not change significantly, yielding a methacrolein conversion rate of 61.7%, methyl methacrylate selectivity of 94.7% and methyl methacrylate formation activity of 7.628 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times, thus confirming that exfoliation and elution of Ni and Au which are catalyst active species as well as elution of Si which is the support component were inhibited. When the catalyst was extracted after reacting for 500 hours and investigated with a scanning electron microscope (SEM), there was hardly any cracking or chipping of the catalyst particles observed. In addition, catalyst pore volume as determined by the nitrogen adsorption method was 0.28 mL/g and average pore diameter was 8 nm.

Next, observation of the catalyst following the reaction with a transmission electron microscope (TEM/STEM) confirmed that nanoparticles having a maximum particle diameter distribution of from 2 to 3 nm (number average particle diameter: 3.0 nm) were loaded on the support. Analysis of composition points by STEM-EDS for each nanoparticle confirmed that nickel and gold were contained in each nanoparticle. The mean value of the ratio of nickel/gold atoms of the composite nanoparticles (number of nanoparticles used for calculation: 50) was 0.85. In addition, when nanoregions of the observed particles were analyzed, nickel was distributed over the gold in all particles, and larger amounts of nickel were detected around the particle edges. In addition, as a result of investigating changes in the electron excitation state of this catalyst by ultraviolet-visible spectroscopy (UV-Vis), surface plasmon absorption peaks originating from gold nanoparticles were not observed in the vicinity of 530 nm.

On the basis of these results, catalyst physical properties and the structure of the nanoparticles of the present embodiment were confirmed to not have changed before and after the reaction.

Example 18

A silica-alumina support having a specific surface area of 110 m²/g was obtained by following the same procedure as in (1) of Example 17 with the exception of adding aluminum nitrate so that the amount of aluminum was 15 mol % based on the total molar amount of silicon and aluminum, and setting the firing temperature to 700° C.

Next, a catalyst was produced in the same manner as (2) of Example 17 with the exception of using the above support and using 4.46 g of nickel nitrate hexahydrate.

The loaded amounts of nickel and gold of the resulting catalyst were 0.25% by mass and 1.43% by mass, respectively. In addition, the atomic ratio of Ni/(Ni+Au) was 0.370 and the atomic ratio of Ni/Al was 0.017.

A broad peak corresponding to gold crystals was present based on the results of powder X-ray diffraction (XRD). The average crystallize size thereof as calculated according to Scherrer's formula was about 3 nm. On the other hand, diffraction patterns originating from nickel were not observed, thus confirming that nickel is present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.452 and the chemical shift (ΔE) was 0.341. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.2 nm) were loaded on the support. An elementary analysis (20 points) was carried out on each observed nanoparticle by an ancillary energy-dispersive X-ray detector (EDX), and nickel and gold were confirmed in all of the particles. The atomic ratio of nickel to gold of these composite particles (mean value) was 0.81.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 58.4%, methyl methacrylate selectivity was 94.7%, and methyl methacrylate formation activity per catalyst unit weight was 7.220 mol/h/kg-cat. Reactivity after 500 hours had elapsed did not change significantly, yielding a methacrolein conversion rate of 58.6%, methyl methacrylate selectivity of 94.9% and methyl methacrylate formation activity of 7.260 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.4 nm, thus demonstrating hardly any change before and after the reaction.

Example 19

300 g of commercially available silica (CARiACT Q-10, Fuji Silysia Chemical, Ltd.) were added to a glass container containing 500 mL of distilled water followed by the gradual addition of 98.5 g of luminum nitrate nonahydrate as an aluminum source to a silica gel solution, dissolving in the silica gel solution and evaporating to dryness over a hot water bath.

The resulting solid was filled to a thickness of about 1 cm into a stainless steel container with the top being open followed by heating in an electric oven from room temperature to 300° C. over the course of 2 hours and then holding at that temperature for 3 hours. After further heating to 600° C. over the course of 2 hours followed by holding at that temperature for 3 hours, the solid was cooled gradually to obtain a silica-alumna support. The amount of aluminum in the resulting support was 5 mol % based on the total molar amount of silicon and aluminum. Specific surface area as determined according to the nitrogen adsorption method was 183 m$^2$/g.

Next, a catalyst was produced in the same manner as (2) of Example 17 with the exception of using the above support and making the amount of nickel nitrate hexahydrate 66.89 g.

The loaded amounts of nickel and gold of the resulting catalyst were 4.50% by mass and 1.44% by mass, respectively. In addition, the atomic ratio of Ni/(Ni+Au) was 0.913 and the atomic ratio of Ni/Al was 0.914.

A broad peak corresponding to gold crystals was present based on the results of powder X-ray diffraction (XRD). The average crystallize size thereof as calculated according to Scherrer's formula was about 3 nm. On the other hand, diffraction patterns originating from nickel were not observed, thus confirming that nickel is present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.403 and the chemical shift (ΔE) was 0.336. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 2.9 nm) were loaded on the support. An elementary analysis (20 points) was carried out on each observed nanoparticle by an ancillary energy-dispersive X-ray detector (EDX), and nickel and gold were confirmed in all of the particles. The atomic ratio of nickel to gold of these composite particles (mean value) was 0.85.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 57.6%, methyl methacrylate selectivity was 93.6%, and methyl methacrylate formation activity per catalyst unit weight was 7.038 mol/h/kg-cat. Reactivity after 500 hours had elapsed did not change significantly, yielding a methacrolein conversion rate of 57.1%, methyl methacrylate selectivity of 93.8% and methyl methacrylate formation activity of 6.992 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.1 nm, thus demonstrating hardly any change before and after the reaction.

Example 20

A commercially available silica-alumina compound (N631 HN manufactured by Nikki Chemical Co., Ltd., amount of alumina based on total molar amount of silicon and aluminum: 30 mol %)) was filled to a thickness of about 1 cm into a stainless steel container with the top being open followed by heating in an electric oven from room temperature to 300° C. over the course of 2 hours and then holding at that temperature for 3 hours. After further heating to 800° C. over the course of 2 hours followed by holding at that temperature for 3 hours, the solid was cooled gradually to obtain the target substance. Specific surface area as determined according to the nitrogen adsorption method was 348 m$^2$/g.

Next, a catalyst was produced in the same manner as (2) of Example 17 with the exception of using the above support. The loaded amounts of nickel and gold of the resulting catalyst were 1.40% by mass and 1.42% by mass, respectively. In addition, the atomic ratio of Ni/(Ni+Au) was 0.768 and the atomic ratio of Ni/Al was 0.046.

A broad peak corresponding to gold crystals was present based on the results of powder X-ray diffraction (XRD). The average crystallize size thereof as calculated according to Scherrer's formula was about 3 nm. On the other hand, diffraction patterns originating from nickel were not observed, thus confirming that nickel is present in an amorphous state.

The chemical state of nickel was presumed to be high-spin divalent nickel based on the results of high-resolution X-ray fluorescence (HRXRF), and was determined to have a chemical state different from that of nickel oxide which is a single compound based on differences in Ni Kα spectra. The full width at half maximum (FWHM) of the Ni Kα spectrum of the catalyst as obtained from the measured spectrum was 3.492 and the chemical shift ($\Delta E$) was 0.329. The full width at half maximum (FWHM) of the Ni Kα spectrum of nickel oxide measured as a standard substance was 3.249 and the chemical shift ($\Delta E$) was 0.344.

In addition, observation of the form of the active species of the catalyst with a transmission electron microscope (TEM/STEM) confirmed that nanoparticles having a maximum particle diameter distribution of 2 to 3 nm (number average particle diameter: 3.0 nm) were loaded on the support. An elementary analysis (20 points) was carried out on each observed nanoparticle by an ancillary energy-dispersive X-ray detector (EDX), and nickel and gold were confirmed in all of the particles. The atomic ratio of nickel to gold of these composite particles (mean value) was 0.80.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst. As a result, the methacrolein conversion rate after reacting for 200 hours was 60.4%, methyl methacrylate selectivity was 94.3%, and methyl methacrylate formation activity per catalyst unit weight was 7.436 mol/h/kg-cat. Reactivity after 500 hours had elapsed did not change significantly, yielding a methacrolein conversion rate of 61.0%, methyl methacrylate selectivity of 94.2% and methyl methacrylate formation activity of 7.501 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.2 nm, thus demonstrating hardly any change before and after the reaction.

Example 21

An aqueous solution in which 4.86 kg of aluminum nitrate nonahydrate and 1.53 kg of rubidium nitrate were dissolved in 5.0 L of pure water was gradually dropped into 20.0 kg of a stirred silica sol solution having a colloidal particle diameter of from 10 to 20 nm held at 15° C. (TX11561 manufactured by Nalco Co., Ltd. ($SiO_2$ content: 30 wt %)) to obtain a mixed slurry of silica sol, aluminum nitrate and rubidium nitrate. Then, the mixed slurry was aged by holding at room temperature for 24 hours. Subsequently, the mixed slurry was spray-dried with a spray dryer set to an outlet temperature of 130° C. to obtain a solid. Next, the resulting solid was filled to a thickness of about 1 cm into a stainless steel container with the top being open followed by heating in an electric oven from room temperature to 400° C. over the course of 2 hours and then holding at that temperature for 3 hours. After further heating to 580° C. over the course of 2 hours followed by holding at that temperature for 3 hours, the solid was cooled gradually to obtain a silica-alumna-rubidium support. The amount of aluminum was 11.5 mol % based on the total molar amount of silicon and aluminum, and the atomic ratio of (alkaline metal+½×alkaline earth metal+⅓×rare earth metal)/Al was 0.80. Specific surface area as determined according to the nitrogen adsorption method was 127 m²/g. The average particle diameter of the support based on the results of measuring with a laser diffraction particle size analyzer was 64 µm. In addition, the shape of the support was found to be nearly spherical based on observations with a scanning electron microscope (SEM).

Next, 1.0 L of a solution containing 14.9 g of nickel nitrate hexahydrate and 13 mL of a 1.3 mol/L aqueous chloroauric acid solution was heated to 90° C. 300 g of the silica-alumina-rubidium support obtained above were placed in this aqueous solution followed by holding at 90° C. while stirring and continuing to stir for 1 hour to deposit the nickel and gold components onto the support.

Next, after allowing to stand undisturbed, removing the supernatant and washing several times with distilled water, the liquid was filtered. After drying the filtrate for 16 hours at 105° C., the product was fired for 3 hours at 500° C. in air to obtain a catalyst loaded with 0.97% by mass of nickel and 0.95% by mass of gold (NiOAu/$SiO_2$—$Al_2O_3$—$Rb_2O$). The atomic ratio of Ni/(Ni+Au) of the resulting catalyst was 0.774, and the atomic ratio of Ni/Al was 0.11 while the atomic ratio of Ni/Rb was 0.137. Based on the results of powder X-ray diffraction (XRD), a diffraction pattern originating from nickel was not observed, thus confirming the nickel to be present in an amorphous state. Although broad as previously described, a peak was present corresponding to gold crystals, and the average crystallite size was 3.0 nm.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.432 and the chemical shift ($\Delta E$) was 0.345. The full width at half maximum (FWHM) of the Ni Kα spectrum of nickel oxide measured as a standard substance was 3.249 and the chemical shift ($\Delta E$) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 2.8 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 1.02.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 240 g. As a result, the methacrolein conversion rate after reacting for 200 hours was 55.3%, methyl methacrylate selectivity was 95.1%, and methyl methacrylate formation activity per catalyst unit weight was 5.721 mol/h/kg-cat. Reactivity after 500 hours had elapsed did not change significantly, yielding a methacrolein conversion rate of 54.9%, methyl methacrylate selectivity of 95.3% and methyl methacrylate formation activity of 5.692 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.2 nm, thus demonstrating hardly any change before and after the reaction.

Example 22

A silica-alumina-strontium support was prepared in the same manner as Example 21 with the exception of using 2.90 kg of strontium nitrate instead of rubidium nitrate. The amount of aluminum was 11.5 mol % based on the total molar amount of silicon and aluminum, and the atomic ratio of (alkaline metal+½×alkaline earth metal+⅓×rare earth metal)/Al was 0.53. Specific surface area as determined according to the nitrogen adsorption method was 138 m²/g. The average particle diameter of the support based on the results of measuring with a laser diffraction particle size analyzer was 62 μm. In addition, the shape of the support was found to be nearly spherical based on observations with a scanning electron microscope (SEM).

Next, a catalyst loaded with 3.98% by mass of nickel and 0.97% by mass of gold (NiOAu/SiO$_2$—Al$_2$O$_3$—SrO) was obtained by a producing a catalyst in the same manner as Example 21 with the exception of using the above support and making the amount of nickel nitrate hexahydrate 59.46 g.

The atomic ratio of Ni/(Ni+Au) of the resulting catalyst was 0.932, and the atomic ratio of Ni/Al was 0.421 while the atomic ratio of Ni/Sr was 0.398.

Based on the results of powder X-ray diffraction (XRD), a broad peak was present corresponding to gold crystals. The average crystallite size as calculated according to Scherrer's formula was about 3 nm. On the other hand, a diffraction pattern originating from nickel was not observed, thus confirming the nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.464 and the chemical shift (ΔE) was 0.339. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.0 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 1.1.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 240 g. As a result, the methacrolein conversion rate after reacting for 200 hours was 52.5%, methyl methacrylate selectivity was 95.0%, and methyl methacrylate formation activity per catalyst unit weight was 5.426 mol/h/kg-cat. Reactivity after 500 hours had elapsed did not change significantly, yielding a methacrolein conversion rate of 52.8%, methyl methacrylate selectivity of 94.9% and methyl methacrylate formation activity of 5.451 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.2 nm, thus demonstrating hardly any change before and after the reaction.

Example 23

A silica-alumina-magnesium-lanthanum support was prepared in the same manner as Example 21 with the exception of making the amount of aluminum nitrate nonahydrate 1.88 kg, and adding 3.5 kg of magnesium nitrate and 1.0 kg of lanthanum chloride salt hydrate in place of rubidium nitrate. The amount of aluminum was 4.8 mol % based on the total molar amount of silicon and aluminum, and the atomic ratio of (alkaline metal+½ alkaline earth metal+⅓ alkaline earth metal)/Al was 1.514. Specific surface area as determined according to the nitrogen adsorption method was 115 m²/g. The average particle diameter of the support based on the results of measuring with a laser diffraction particle size analyzer was 62 μm. In addition, the shape of the support was found to be nearly spherical based on observations with a scanning electron microscope (SEM).

Next, a catalyst was produced in the same manner as Example 21 with the exception of using the above support and making the amount of nickel nitrate hexahydrate 4.46 g.

The loaded amounts of nickel and gold of the resulting catalyst were 0.25% by mass and 1.02% by mass, respectively. In addition, the atomic ratio of Ni/(Ni+Au) of the resulting catalyst was 0.451, and the atomic ratio of Ni/Al was 0.064 while the atomic ratio of Ni/(Mg+La) was 0.061.

Based on the results of powder X-ray diffraction (XRD), a broad peak was present corresponding to gold crystals. The average crystallite size as calculated according to Scherrer's formula was about 3 nm. On the other hand, a diffraction pattern originating from nickel was not observed, thus confirming the nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.493 and the chemical shift (ΔE) was 0.335. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.2 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 1.09.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 240 g. As a result, the methacrolein conversion rate after reacting for 200 hours was 53.6%, methyl methacrylate selectivity was 95.3%, and methyl methacrylate formation activity per catalyst unit weight was 5.557 mol/h/kg-cat. Reactivity after 500 hours had elapsed did not change significantly, yielding a methacrolein conversion rate of 53.3%, methyl methacrylate selectivity of 95.2% and methyl methacrylate formation activity of 5.520 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.2 nm, thus demonstrating hardly any change before and after the reaction.

Table 4 shows the physical properties of the catalysts for producing carboxylic acid esters of Examples 17 to 23.

TABLE 4

| No. | Catalyst | Silica and Alumina Compositions (mol %) | | Loaded Amounts of Ni and Au (% by mass) | | Ratios of Catalyst Constituent Elements (atomic ratios) | | |
|---|---|---|---|---|---|---|---|---|
| | | Si | Al | Ni | Au | Ni/(Ni + Au) | Ni/Al | Ni/basic metal |
| Example 17 | NiOAu/SiO$_2$—Al$_2$O$_3$ | 90.0 | 10.0 | 1.43 | 1.45 | 0.768 | 0.144 | — |
| Example 18 | NiOAu/SiO$_2$—Al$_2$O$_3$ | 85.0 | 15.0 | 0.25 | 1.43 | 0.370 | 0.017 | — |
| Example 19 | NiOAu/SiO$_2$—Al$_2$O$_3$ | 95.0 | 5.0 | 4.50 | 1.44 | 0.913 | 0.914 | — |
| Example 20 | NiOAu/SiO$_2$—Al$_2$O$_3$ | 70.0 | 30.0 | 1.40 | 1.42 | 0.768 | 0.046 | — |
| Example 21 | NiOAu/SiO$_2$—Al$_2$O$_3$—Rb$_2$O | 88.5 | 11.5 | 0.97 | 0.95 | 0.774 | 0.110 | 0.137 |
| Example 22 | NiOAu/SiO$_2$—Al$_2$O$_3$—SrO | 88.5 | 11.5 | 3.98 | 0.97 | 0.932 | 0.421 | 0.398 |
| Example 23 | NiOAu/SiO$_2$—Al$_2$O$_3$—MgO—La$_2$O$_3$ | 95.2 | 4.8 | 0.25 | 1.02 | 0.451 | 0.064 | 0.061 |

Example 24

An ethyl acrylate formation reaction was carried out using the same procedure and under the same reaction conditions as (3) of Example 17 with the exception of using the catalyst prepared in (2) of Example 17 (NiOAu/SiO$_2$—Al$_2$O$_3$) and reacting acrolein instead of methacrolein and reacting ethanol instead of methanol.

As a result, the acrolein conversion rate after reacting for 200 hours was 71.2%, ethyl acrylate selectivity was 96.2%, and ethyl acrylate formation activity per catalyst unit weight was 8.942 mol/h/kg-cat. Reactivity after 500 hours had elapsed did not change significantly, yielding an acrolein conversion rate of 71.5%, ethyl acrylate selectivity of 96.1% and ethyl acrylate formation activity of 8.970 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.4 nm, thus demonstrating hardly any change before and after the reaction.

Example 25

(1) Support Production

An aqueous solution in which 3.75 kg of aluminum nitrate nonahydrate, 2.56 kg of magnesium nitrate and 540 g of 60% nitric acid were dissolved in 5.0 L of pure water was gradually dropped into 20.0 kg of a stirred silica sol solution having a colloidal particle diameter of from 10 to 20 nm held at 15° C. (Snowtex N-30 manufactured by Nissan Chemical Industries, Ltd. ($SiO_2$ content: 30% by mass)) to obtain a mixed slurry of silica sol, aluminum nitrate and magnesium nitrate. Subsequently, the mixed slurry was aged by holding at 50° C. for 24 hours. After cooling to room temperature, the mixed slurry was spray-dried with a spray dryer set to an outlet temperature of 130° C. to obtain a solid.

Next, the resulting solid was filled to a thickness of about 1 cm into a stainless steel container with the top being open followed by heating in an electric oven from room temperature to 300° C. over the course of 2 hours and then holding at that temperature for 3 hours. After further heating to 600° C. over the course of 2 hours followed by holding at that temperature for 3 hours, the solid was cooled gradually to obtain a support. The amounts of silicon, aluminum and magnesium in the resulting support were 83.3 mol %, 8.3 mol % and 8.3 mol %, respectively, based on the total molar amount of silicon, aluminum and magnesium. Specific surface area as determined according to the nitrogen adsorption method was 148 $m^2$/g, pore volume was 0.26 mL/g, and average pore diameter was 8 nm. The average particle diameter of the support based on the results of measuring with a laser diffraction particle size analyzer was 64 μm. In addition, the shape of the support was found to be nearly spherical based on observations with a scanning electron microscope (SEM).

(2) Catalyst Preparation 1.0 L of a solution containing 23.78 g of nickel nitrate hexahydrate and 19 mL of a 1.3 mol/L aqueous chloroauric acid solution was heated to 90° C. 300 g of the silica-alumina-magnesia support obtained above were placed in this aqueous solution followed by holding at 90° C. while stirring and then continuing to stir for 1 hour to deposit the nickel and gold components onto the support.

Next, after allowing to stand undisturbed, removing the supernatant and washing several times with distilled water, the liquid was filtered. After drying the filtrate for 16 hours at 105° C., the product was fired for 3 hours at 500° C. in air to obtain a catalyst loaded with 1.52% by mass of nickel and 1.49% by mass of gold (NiOAu/$SiO_2$—$Al_2O_3$—MgO). The atomic ratio of Ni/(Ni+Au) of the resulting catalyst was 0.774, the atomic ratio of Ni/Al was 0.179, and the atomic ratio of Ni/Mg was 0.179. Specific surface area as determined by the nitrogen adsorption method was 150 $m^2$/g, pore volume was 0.28 mL/g, and average pore diameter was 5 nm.

The average particle diameter of the catalyst based on the results of measuring with a laser diffraction particle size analyzer was 65 μm. The shape of the catalyst was found to be nearly spherical based on observations with a scanning electron microscope (SEM).

Based on the results of powder X-ray diffraction (XRD), a diffraction pattern originating from nickel was not observed, and the nickel was confirmed to be present in an amorphous state. On the other hand, although not able to be defined as a well-defined peak, a broad peak was present corresponding to gold crystals. Although the value of this peak was close to the powder X-ray diffraction detection limit (2 nm), calculation of the average crystallite size using Scherrer's formula yielded a value of about 3 nm.

With respect to the chemical state of the Ni, the valence was confirmed to be 2 based on the results of X-ray photoelectron spectroscopy (XPS). Moreover, the chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.489 and the chemical shift (ΔE) was 0.340. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.0 nm) were loaded on the support. Observation of enlarged images of the nanoparticles demonstrated that the nanoparticles had a lattice pattern corresponding to the lattice spacing of Au (111). Analysis of composition points by STEM-EDS for each nanoparticle confirmed that gold and nickel were contained in each nanoparticle. The mean value of the ratio of nickel/gold atoms of the composite nanoparticles (number of nanoparticles used for calculation: 50) was 0.85. Moreover, when nanoregions of the observed particles were analyzed, nickel was distributed over the gold in all particles, and larger amounts of nickel were detected around the particle edges.

Next, as a result of investigating changes in the electron excitation state of this catalyst by ultraviolet-visible spectroscopy (UV-Vis), surface plasmon absorption peaks originating from gold nanoparticles were not observed in the vicinity of 530 nm, while broad absorbance attributable to $NiO_2$ was observed over a wavelength range from 200 to 800 nm.

On the basis of these results, nanoparticles contained in the catalyst according to the present embodiment were confirmed to have a form in which the surface of gold nanoparticles is covered with oxidized nickel, and have a different surface electron state than that of gold nanoparticles comprised of a single metal species.

(3) Synthesis of Carboxylic Acid Ester

A reaction was carried out in the same manner as (3) of Example 17 using the catalyst obtained above (NiOAu/$SiO_2$—$Al_2O_3$—MgO). As a result, the methacrolein conversion rate after reacting for 200 hours was 65.3%, methyl methacrylate selectivity was 96.1%, and methyl methacrylate formation activity per catalyst unit weight was 8.192 mol/h/kg-cat. Reactivity after 500 hours had elapsed did not change significantly, yielding a methacrolein conversion rate of 65.1%, methyl methacrylate selectivity of 96.0% and methyl methacrylate formation activity of 8.159 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times, thus confirming that exfoliation and elution of nickel and gold which are catalyst active species as well as elution of silica which is the support component were inhibited. When the catalyst was extracted after reacting for 500 hours and investigated with a scanning electron microscope (SEM), there was hardly any cracking or chipping of the catalyst particles observed. In addition, catalyst pore volume as determined by the nitrogen adsorption method was 0.27 mL/g and average pore diameter was 5 nm. Moreover, observation of the catalyst following the reaction with a transmission electron microscope (TEM/STEM) confirmed that nanoparticles having a maximum particle diameter distribution of from 2 to 3 nm (number average particle diameter: 3.2 nm) were loaded on the support. Analysis of composition points by STEM-EDS for each nanoparticle confirmed that nickel and gold were contained in each nanoparticle. The mean value of the ratio of nickel/gold atoms of the composite nanoparticles (number of nanoparticles used for calculation: 50) was 0.82. Moreover, when nanoregions of the observed particles were analyzed, nickel was distributed over the gold in all particles, and larger amounts of nickel were detected around the particle edges. Next, as a result of investigating changes in the electron excitation state of this catalyst by ultraviolet-visible spectroscopy (UV-Vis), surface plasmon absorption peaks originating from gold nanoparticles were not observed in the vicinity of 530 nm.

On the basis of these results, catalyst physical properties and the structure of the nanoparticles of the present embodiment were confirmed to not have changed before and after the reaction.

Example 26

A support having a specific surface area of 155 m$^2$/g was obtained in the same manner as (1) of Example 25 with the exception of adding aluminum nitrate and magnesium nitrate to a silica sol such that the amounts of aluminum and magnesium contained in the support were 13.6 mol % and 4.3 mol %, respectively, based on the total molar amount of silicon, aluminum and magnesium, and making the firing temperature 700° C.

Next, a catalyst was prepared in the same manner as (2) of Example 25 with the exception of using the above support and making the amount of nickel nitrate hexahydrate 3.72 g.

The loaded amounts of nickel and gold of the resulting catalyst were 0.20% by mass and 1.48% by mass, respectively. In addition, the atomic ratio of Ni/(Ni+Au) was 0.312, and the atomic ratio of Ni/Al was 0.014 while the atomic ratio of Ni/Mg was 0.046. Based on the results of powder X-ray diffraction (XRD), a diffraction pattern originating from nickel was not observed, thus confirming nickel to be present in an amorphous state. Although broad as previously described, a peak was present corresponding to gold crystals, and the average crystallite size was calculated to be 3.0 nm.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.480 and the chemical shift (ΔE) was 0.334. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.3 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.79.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 64.4%, methyl methacrylate selectivity was 95.8%, and methyl methacrylate formation activity per catalyst unit weight was 8.054 mol/h/kg-cat. Reactivity after 500 hours had elapsed did not change significantly, yielding a methacrolein conversion rate of 64.6%, methyl methacrylate selectivity of 95.7% and methyl methacrylate formation activity of 8.071 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.4 nm, thus demonstrating hardly any change before and after the reaction.

Example 27

A support having a specific surface area of 138 m$^2$/g was obtained in the same manner as (1) of Example 25 with the exception of adding aluminum nitrate and magnesium nitrate to a silica sol such that the amounts of aluminum and magnesium contained in the support were 22.3 mol % and 5.6 mol %, respectively, based on the total molar amount of silicon, aluminum and magnesium, and making the firing temperature 800° C.

Next, a catalyst was prepared in the same manner as (2) of Example 25 with the exception of using the above support and making the amount of nickel nitrate hexahydrate 77.29 g.

The loaded amounts of nickel and gold of the resulting catalyst were 5.0% by mass and 1.49% by mass, respectively. In addition, the atomic ratio of Ni/(Ni+Au) was 0.918, and the atomic ratio of Ni/Al was 0.217 while the atomic ratio of Ni/Mg was 0.858.

Based on the results of powder X-ray diffraction (XRD), a broad peak was present corresponding to gold crystals. The average crystallite size as calculated according to Scherrer's formula was about 3.0 nm. On the other hand, a diffraction pattern originating from nickel was not observed, thus confirming nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.479 and the chemical shift (ΔE) was 0.327. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/

STEM) confirmed that nanoparticles having a maximum particle diameter distribution of from 2 to 3 nm (number average particle diameter: 3.1 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.93.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 64.1%, methyl methacrylate selectivity was 95.6%, and methyl methacrylate formation activity per catalyst unit weight was 8.0 mol/h/kg-cat. Reactivity after 500 hours had elapsed did not change significantly, yielding a methacrolein conversion rate of 63.9%, methyl methacrylate selectivity of 95.7% and methyl methacrylate formation activity of 7.983 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.2 nm, thus demonstrating hardly any change before and after the reaction.

Example 28

A support having a specific surface area of 123 m$^2$/g was obtained in the same manner as (1) of Example 25 with the exception of adding aluminum nitrate and magnesium nitrate to a silica sol such that the amounts of aluminum and magnesium contained in the support were 36.6 mol % and 17.2 mol %, respectively, based on the total molar amount of silicon, aluminum and magnesium, and making the firing temperature 800° C.

Next, a catalyst was prepared in the same manner as (2) of Example 25 with the exception of using the above support, making the amount of nickel nitrate hexahydrate 16.35 g and making the amount of 1.3 mol/L aqueous chloroauric acid solution 13 mL.

The loaded amounts of nickel and gold of the resulting catalyst were 1.0% by mass and 0.90% by mass, respectively. In addition, the atomic ratio of Ni/(Ni+Au) was 0.789, and the atomic ratio of Ni/Al was 0.025 while the atomic ratio of Ni/Mg was 0.053.

Based on the results of powder X-ray diffraction (XRD), a broad peak was present corresponding to gold crystals. The average crystallite size as calculated according to Scherrer's formula was about 3 nm. On the other hand, a diffraction pattern originating from nickel was not observed, thus confirming nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.487 and the chemical shift (ΔE) was 0.344. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 2.8 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 1.03.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 240 g. As a result, the methacrolein conversion rate after reacting for 200 hours was 63.4%, methyl methacrylate selectivity was 95.3%, and methyl methacrylate formation activity per catalyst unit weight was 6.573 mol/h/kg-cat. Reactivity after 500 hours had elapsed did not change significantly, yielding a methacrolein conversion rate of 63.6%, methyl methacrylate selectivity of 95.4% and methyl methacrylate formation activity of 6.601 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.0 nm, thus demonstrating hardly any change before and after the reaction.

Example 29

Sulfuric acid was added to 10 kg of sodium silicate solution no. 3 (SiO$_2$: 28 to 30% by mass, Na$_2$O: 9 to 10% by mass) to adjust the pH to 9 followed by the addition of Al$_2$(SO$_4$)$_3$ to adjust the pH to 2. Moreover, sodium aluminate was then added to adjust the pH to 5 to 5.5 after which a portion thereof was dehydrated to obtain a hydrogel containing about 10% by mass of silica-alumina. After spray drying with a spray dryer at 130° C., the hydrogel was washed until the Na$_2$O content was 0.02% by mass and the SO$_4$ content was 0.5% by mass or less. This was then mixed with 300 g of MgO in the form of a slurry, heat-treated for 3 hours at 80° C., filtered and washed followed by drying for 6 hours at 110° C., heating over the course of 3 hours to 700° C., holding at that temperature for 3 hours and then cooling gradually. The resulting support contained 79.1 mol %, 14.7 mol % and 6.3 mol % of silicon, aluminum and magnesium, respectively, based on the total molar amount of silicon, aluminum and magnesium. Specific surface area as determined according to the nitrogen adsorption method was 223 m$^2$/g. The average particle diameter of the support was 60 μm based on results obtained with a laser diffraction particle size analyzer. By the observation with a scanning electron microscope (SEM), it was found that the support was almost spherical.

Next, a catalyst was prepared in the same manner as (2) of Example 25 with the exception of using the above support, making the amount of nickel nitrate hexahydrate 47.56 g and making the amount of 1.3 mol/L aqueous chloroauric acid solution 13 mL.

The loaded amounts of nickel and gold of the resulting catalyst were 3.02% by mass and 0.95% by mass, respectively. In addition, the atomic ratio of Ni/(Ni+Au) was 0.914, and the atomic ratio of Ni/Al was 0.202 while the atomic ratio of Ni/Mg was 0.471.

Based on the results of powder X-ray diffraction (XRD), a broad peak was present corresponding to gold crystals. The average crystallite size as calculated according to Scherrer's formula was about 3 nm. On the other hand, a diffraction pattern originating from nickel was not observed, thus confirming nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.490 and the chemical shift ($\Delta E$) was 0.336. The full width at half maximum (FWHM) of the Ni Kα spectrum of nickel oxide measured as a standard substance was 3.249 and the chemical shift ($\Delta E$) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 2.9 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 1.12.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 240 g. As a result, the methacrolein conversion rate after reacting for 200 hours was 66.2%, methyl methacrylate selectivity was 95.8%, and methyl methacrylate formation activity per catalyst unit weight was 6.899 mol/h/kg-cat. Reactivity after 500 hours had elapsed did not change significantly, yielding a methacrolein conversion rate of 66.1%, methyl methacrylate selectivity of 95.9% and methyl methacrylate formation activity of 6.896 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.0 nm, thus demonstrating hardly any change before and after the reaction.

Example 30

A support having a specific surface area of 167 m²/g was obtained in the same manner as (1) of Example 25 with the exception of adding aluminum nitrate and magnesium hydroxide to a silica sol such that the amounts of aluminum and magnesium contained in the support were 10.2 mol % and 7.2 mol %, respectively, based on the total molar amount of silicon, aluminum and magnesium, and making the firing temperature 600° C.

Next, a catalyst was prepared in the same manner as (2) of Example 25 with the exception of using the above support, making the amount of nickel nitrate hexahydrate 112.97 g and making the amount of 1.3 mol/L aqueous chloroauric acid solution 38 mL.

The loaded amounts of nickel and gold of the resulting catalyst were 7.50% by mass and 3.10% by mass, respectively. In addition, the atomic ratio of Ni/(Ni+Au) was 0.89, and the atomic ratio of Ni/Al was 0.724 while the atomic ratio of Ni/Mg was 1.0.

Based on the results of powder X-ray diffraction (XRD), a broad peak was present corresponding to gold crystals. The average crystallite size as calculated according to Scherrer's formula was about 5 nm. On the other hand, a diffraction pattern originating from nickel was not observed, thus confirming nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.487 and the chemical shift ($\Delta E$) was 0.333. The full width at half maximum (FWHM) of the Ni Kα spectrum of nickel oxide measured as a standard substance was 3.249 and the chemical shift ($\Delta E$) was 0.344.

In addition, observation of the form of the active species of the catalyst with a transmission electron microscope (TEM/STEM) confirmed that nanoparticles having a maximum particle diameter distribution of from 4 to 5 nm (number average particle diameter: 4.2 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.71.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 100 g. As a result, the methacrolein conversion rate after reacting for 200 hours was 63.4%, methyl methacrylate selectivity was 95.2%, and methyl methacrylate formation activity per catalyst unit weight was 15.759 mol/h/kg-cat. Reactivity after 500 hours had elapsed did not change significantly, yielding a methacrolein conversion rate of 63.2%, methyl methacrylate selectivity of 94.9% and methyl methacrylate formation activity of 15.66 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 4.2 nm, thus demonstrating hardly any change before and after the reaction.

Example 31

A support having a specific surface area of 134 m$^2$/g was obtained in the same manner as (1) of Example 25 with the exception of adding aluminum nitrate and magnesium hydroxide to a silica sol such that the amounts of aluminum and magnesium contained in the support were 15.1 mol % and 37.5 mol %, respectively, based on the total molar amount of silicon, aluminum and magnesium, and making the firing temperature 650° C.

Next, a catalyst was prepared in the same manner as (2) of Example 25 with the exception of using the above support, making the amount of nickel nitrate hexahydrate 46.0 g and making the amount of 1.3 mol/L aqueous chloroauric acid solution 38 mL.

The loaded amounts of nickel and gold of the resulting catalyst were 3.0% by mass and 2.99% by mass, respectively. In addition, the atomic ratio of Ni/(Ni+Au) was 0.771, and the atomic ratio of Ni/Al was 0.174 while the atomic ratio of Ni/Mg was 0.07.

Based on the results of powder X-ray diffraction (XRD), a broad peak was present corresponding to gold crystals. The average crystallite size as calculated according to Scherrer's formula was about 5 nm. On the other hand, a diffraction pattern originating from nickel was not observed, thus confirming nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.478 and the chemical shift (ΔE) was 0.334. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 4 to 6 nm (number average particle diameter: 5.2 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.65.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 100 g. As a result, the methacrolein conversion rate after reacting for 200 hours was 61.3%, methyl methacrylate selectivity was 95.4%, and methyl methacrylate formation activity per catalyst unit weight was 15.269 mol/h/kg-cat. Reactivity after 500 hours had elapsed did not change significantly, yielding a methacrolein conversion rate of 61.2%, methyl methacrylate selectivity of 95.6% and methyl methacrylate formation activity of 15.276 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 5.1 nm, thus demonstrating hardly any change before and after the reaction.

Example 32

A support having a specific surface area of 144 m$^2$/g was obtained in the same manner as (1) of Example 25 with the exception of adding aluminum nitrate and magnesium nitrate to a silica sol such that the amounts of aluminum and magnesium contained in the support were 5.6 mol % and 4.4 mol %, respectively, based on the total molar amount of silicon, aluminum and magnesium.

Next, a catalyst was prepared in the same manner as (2) of Example 25 with the exception of using the above support, making the amount of nickel nitrate hexahydrate 5.94 g and making the amount of 1.3 mol/L aqueous chloroauric acid solution 12 mL.

The loaded amounts of nickel and gold of the resulting catalyst were 0.30% by mass and 0.90% by mass, respectively. In addition, the atomic ratio of Ni/(Ni+Au) was 0.528, and the atomic ratio of Ni/Al was 0.053 while the atomic ratio of Ni/Mg was 0.069.

Based on the results of powder X-ray diffraction (XRD), a broad peak was present corresponding to gold crystals. The average crystallite size as calculated according to Scherrer's formula was about 3 nm. On the other hand, a diffraction pattern originating from nickel was not observed, thus confirming nickel to be present in an amorphous state.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.411 and the chemical shift (ΔE) was 0.331. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of 2 to 3 nm (number average particle diameter: 2.8 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 1.15.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 with the exception of using this catalyst and making the amount of catalyst 240 g. As a result, the methacrolein conversion rate after reacting for 200 hours was 62.1%, methyl methacrylate selectivity was 95.2%, and methyl methacrylate formation activity per catalyst unit weight was 6.432 mol/h/kg-cat. Reactivity after 500 hours had elapsed did not change significantly, yielding a methacrolein conversion rate of 62.3%, methyl methacrylate selectivity of 95.1% and methyl methacrylate formation activity of 6.445 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.0 nm, thus demonstrating hardly any change before and after the reaction.

Table 5 shows the physical properties of the catalysts for producing carboxylic acid esters of Examples 25 to 32.

As a result, the acrolein conversion rate after reacting for 200 hours was 75.4%, ethyl acrylate selectivity was 97.3%, and ethyl acrylate formation activity per catalyst unit weight was 9.577 mol/h/kg-cat. Reactivity after 500 hours had elapsed did not change significantly, yielding an acrolein conversion rate of 75.2%, ethyl acrylate selectivity of 97.4% and ethyl acrylate formation activity of 9.562 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.1 nm, thus demonstrating hardly any change before and after the reaction.

Example 34

A methyl glycolate formation reaction was carried out using the same procedure and reaction conditions as (3) of Example 17 with the exception of using the catalyst prepared in Example 25 (NiOAu/SiO$_2$—Al$_2$O$_3$—MgO) and reacting ethylene glycol instead of methacrolein.

As a result, the ethylene glycol conversion rate after reacting for 200 hours was 52.4%, methyl glycolate selectivity was 92.4%, and methyl glycolate formation activity per catalyst unit weight was 6.321 mol/h/kg-cat. Reactivity after 500 hours had elapsed did not change significantly, yielding an

TABLE 5

| No. | Catalyst | Support Elementary Composition (mol %) | | | Loaded Amounts of Ni and Au (% by mass) | | Ratios of Catalyst Constituent Elements (Atomic Ratios) | | |
|---|---|---|---|---|---|---|---|---|---|
| | | Si | Al | Mg | Ni | Au | Ni/(Ni + Au) | Ni/Al | Ni/Mg |
| Example 25 | NiOAu/SiO$_2$—Al$_2$O$_3$—MgO | 83.3 | 8.3 | 8.3 | 1.52 | 1.49 | 0.774 | 0.179 | 0.179 |
| Example 26 | NiOAu/SiO$_2$—Al$_2$O$_3$—MgO | 82.0 | 13.6 | 4.3 | 0.20 | 1.48 | 0.312 | 0.014 | 0.046 |
| Example 27 | NiOAu/SiO$_2$—Al$_2$O$_3$—MgO | 72.0 | 22.3 | 5.6 | 5.00 | 1.49 | 0.918 | 0.217 | 0.858 |
| Example 28 | NiOAu/SiO$_2$—Al$_2$O$_3$—MgO | 46.2 | 36.6 | 17.2 | 1.00 | 0.90 | 0.789 | 0.025 | 0.053 |
| Example 29 | NiOAu/SiO$_2$—Al$_2$O$_3$—MgO | 79.1 | 14.7 | 6.3 | 3.02 | 0.95 | 0.914 | 0.202 | 0.471 |
| Example 30 | NiOAu/SiO$_2$—Al$_2$O$_3$—MgO | 82.6 | 10.2 | 7.2 | 7.50 | 3.10 | 0.890 | 0.724 | 1.030 |
| Example 31 | NiOAu/SiO$_2$—Al$_2$O$_3$—MgO | 47.4 | 15.1 | 37.5 | 3.00 | 2.99 | 0.771 | 0.174 | 0.070 |
| Example 32 | NiOAu/SiO$_2$—Al$_2$O$_3$—MgO | 90.0 | 5.6 | 4.4 | 0.30 | 0.90 | 0.528 | 0.053 | 0.069 |

Example 33

An ethyl acrylate formation reaction was carried out using the same procedure and reaction conditions as (3) of Example 17 with the exception of using the catalyst prepared in Example 25 (NiOAu/SiO$_2$—Al$_2$O$_3$—MgO), reacting acrolein instead of methacrolein, and reacting ethanol instead of methanol.

ethylene glycol conversion rate of 52.6%, methyl glycolate selectivity of 92.3% and methyl glycolate formation activity of 6.33 mol/h/kg-cat.

In addition, when the concentrations of Ni, Au and Si ions in the reaction solution were analyzed by ICP-MS at 200 and 500 hours after the start of the reaction, Ni and Au were 0.1 ppm or less at both times and Si was 1 ppm or less at both times. When the catalyst was extracted after reacting for 500 hours and investigated with a scanning electron microscope (SEM), there was hardly any cracking or chipping of the catalyst particles observed. In addition, the number average particle diameter of the composite nanoparticles as determined with a transmission electron microscope (TEM) was 3.2 nm, thus demonstrating hardly any change before and after the reaction.

Example 35

A catalyst loaded with 1.45% by mass of nickel and 1.44% by mass of gold (NiOAu/SiO$_2$/K) was obtained by producing a catalyst in the same manner as (2) of Example 17 with the exception of using a support in which 4% by mass of potassium was impregnated into commercially available silica (CARiACT Q-10, Fuji Silysia Chemical, Ltd.) and firing at 600° C. The atomic ratio of Ni/(Ni+Au) of the resulting catalyst was 0.772. Based on the results of powder X-ray diffraction (XRD) of this catalyst, a diffraction pattern originating from nickel was not observed, thus confirming nickel to be present in an amorphous state. On the other hand, a broad peak was present corresponding to gold crystals, and the average crystallite size as calculated according to Scherrer's formula was about 3 nm.

The chemical state of nickel was presumed to be high-spin divalent nickel based on the results of high-resolution X-ray fluorescence (HRXRF), and the Ni Kα spectrum closely matched that of nickel oxide which is a single compound. The full width at half maximum (FWHM) of the Ni Kα spectrum of the catalyst as obtained from the measured spectrum was 0.325 and the chemical shift (ΔE) was 0.331. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.2 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.86.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 45.2%, methyl methacrylate selectivity was 92.5%, and methyl methacrylate formation activity per catalyst unit weight was 5.458 mol/h/kg-cat. Reactivity after 500 hours had elapsed demonstrated decreases in reaction activity and selectivity, yielding a methacrolein conversion rate of 40.4%, methyl methacrylate selectivity of 91.4% and methyl methacrylate formation activity of 4.821 mol/h/kg-cat.

In addition, when the concentrations of Ni, Au and Si ions in the reaction solution were analyzed by ICP-MS at 200 and 500 hours after the start of the reaction, the concentrations of Ni were 5 ppm and 3 ppm, those of Au were 1 ppm and 0.6 ppm, and those of Si were 10 ppm and 7 ppm, thus demonstrating exfoliation and elution of Ni, Au and Si. When the catalyst was extracted after reacting for 500 hours and investigated with a scanning electron microscope (SEM), cracking and chipping were observed in a portion of the catalyst.

In addition, the number average particle diameter of the composite nanoparticles as determined with a transmission electron microscope (TEM) was 4.6 nm, thus observing sintering of the composite nanoparticles.

Example 36

A catalyst loaded with 1.49% by mass of nickel and 1.51% by mass of gold (NiOAu/γAl$_2$O$_3$) was obtained by producing a catalyst in the same manner as (2) of Example 17 with the exception of using commercially available γ-alumina (Neobead, Mizusawa Industrial Chemicals, Ltd). The atomic ratio of Ni/(Ni+Au) of the resulting catalyst was 0.768. Based on the results of powder X-ray diffraction (XRD) of this catalyst, a diffraction pattern originating from nickel was not observed, thus confirming nickel to be present in an amorphous state. On the other hand, a broad peak was present corresponding to gold crystals, and the average crystallite size as calculated according to Scherrer's formula was about 3 nm.

The chemical state of nickel was presumed to be high-spin divalent nickel based on the results of high-resolution X-ray fluorescence (HRXRF), and was determined to have a chemical state different from that of nickel oxide which is a single compound, based on differences in Ni Kα spectra. The full width at half maximum (FWHM) of the Ni Kα spectrum of the catalyst as obtained from the measured spectrum was 3.350 and the chemical shift (ΔE) was 0.334. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.1 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.89.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 47.2%, methyl methacrylate selectivity was 92.8%, and methyl methacrylate formation activity per catalyst unit weight was 5.718 mol/h/kg-cat. Reactivity after 500 hours had elapsed demonstrated decreases in reaction activity and selectivity, yielding a methacrolein conversion rate of 41.4%, methyl methacrylate selectivity of 91.5% and methyl methacrylate formation activity of 4.945 mol/h/kg-cat.

In addition, when the concentrations of Ni, Au and Al ions in the reaction solution were analyzed by ICP-MS at 200 and 500 hours after the start of the reaction, the concentrations of Ni were 3 ppm and 2 ppm, those of Au were 0.9 ppm and 0.7 ppm, and those of Al were 10 ppm and 8 ppm, thus demonstrating exfoliation and elution of Ni, Au and Al. When the catalyst was extracted after reacting for 500 hours and investigated with a scanning electron microscope (SEM), cracking and chipping were observed in a portion of the catalyst. In addition, the number average particle diameter of the composite nanoparticles as determined with a transmission electron microscope (TEM) was 4.2 nm, thus demonstrating sintering of the composite nanoparticles.

Example 37

A catalyst loaded with 1.50% by mass of nickel and 1.52% by mass of gold (NiOAu/SiO$_2$—TiO$_2$) was obtained by producing a catalyst in the same manner as (2) of Example 17 with the exception of using the silica-titania used as a support in Example 5 for the support. The atomic ratio of Ni/(Ni+Au) of the resulting catalyst was 0.768. Based on the results of powder X-ray diffraction (XRD) of this catalyst, a diffraction pattern originating from nickel was not observed, thus confirming nickel to be present in an amorphous state. On the other hand, a broad peak was present corresponding to gold crystals, and the average crystallite size as calculated according to Scherrer's formula was about 3 nm.

The chemical state of nickel was presumed to be high-spin divalent nickel based on the results of high-resolution X-ray fluorescence (HRXRF), and the Ni Kα spectrum closely matched that of nickel oxide which is a single compound. The full width at half maximum (FWHM) of the Ni Kα spectrum of the catalyst as obtained from the measured spectrum was 3.252 and the chemical shift (ΔE) was 0.330. The full width at half maximum (FWHM) of the Ni Kα spectrum of nickel oxide measured as a standard substance was 3.249 and the chemical shift (ΔE) was 0.344.

In addition, observation of the form of the active species of the catalyst with a transmission electron microscope (TEM/STEM) confirmed that nanoparticles having a maximum particle diameter distribution of from 2 to 3 nm (number average particle diameter: 3.2 nm) were loaded on the support. An elementary analysis (20 points) was carried out on each observed nanoparticle by an ancillary energy-dispersive X-ray detector (EDX), and nickel and gold were confirmed to be contained in all of the particles. The atomic ratio of nickel to gold of these composite particles (mean value) was 0.81.

Moreover, as a result of investigating changes in the electron excitation state of this catalyst by ultraviolet-visible spectroscopy (UV-Vis), surface plasmon absorption peaks originating from gold nanoparticles were not observed (at about 530 nm).

A reaction was carried out in the same manner as (3) of Example 17 using this catalyst. As a result, the methacrolein conversion rate after reacting for 200 hours was 55.3%, methyl methacrylate selectivity was 92.8%, and methyl methacrylate formation activity per catalyst unit weight was 6.699 mol/h/kg-cat. Reactivity after 500 hours had elapsed demonstrated decreases in reaction activity and selectivity, yielding a methacrolein conversion rate of 48.8%, methyl methacrylate selectivity of 92.1% and methyl methacrylate formation activity of 5.867 mol/h/kg-cat.

In addition, when the concentrations of Ni, Au and Si ions in the reaction solution were analyzed by ICP-MS at 200 and 500 hours after the start of the reaction, the concentrations of Ni were 8.0 ppm and 3.0 ppm, those of Au were 1.3 ppm and 0.9 ppm, and those of Si were 8.0 ppm and 6.0 ppm, thus demonstrating exfoliation and elution of Ni, Au and Si. When the catalyst was extracted after reacting for 500 hours and investigated with a scanning electron microscope (SEM), cracking and chipping were observed in a portion of the catalyst. In addition, catalyst pore volume as determined according to the nitrogen adsorption method was 0.46 mL/g and average pore diameter was 15 nm. The number average particle diameter of the composite nanoparticles as determined with a transmission electron microscope (TEM) was 4.4 nm, thus demonstrating increased catalyst pore diameter and sintering of the composite nanoparticles.

Comparative Example 10

A catalyst loaded with 1.48% by mass of gold (Au/SiO$_2$—Al$_2$O$_3$) was obtained by producing a catalyst in the same manner as (2) of Example 17 with the exception of using the silica-alumina support prepared in (1) of Example 17 for the support and not adding nickel nitrate hexahydrate. Based on the results of powder X-ray diffraction (XRD) of this catalyst, a broad peak was present corresponding to gold crystals. The average crystallite size as calculated according to Scherrer's formula was about 3 nm. When the form of the gold particles was observed with a transmission electron microscope (TEM), gold particles having a number average particle diameter of 3.5 nm were confirmed to be loaded onto the support. In addition, the specific surface area of the catalyst was 148 m$^2$/g, the pore volume of the catalyst as determined by the nitrogen adsorption method was 0.29 mL/g, and the average pore diameter was 8 nm. Moreover, as a result of investigating changes in the electron excitation state of this catalyst by ultraviolet-visible spectroscopy (UV-Vis), a surface plasmon absorption peak originating from gold nanoparticles was observed (at about 530 nm).

A reaction was carried out in the same manner as (3) of Example 17 using this catalyst. As a result, the methacrolein conversion rate after reacting for 200 hours was 25.3%, methyl methacrylate selectivity was 80.5%, and methyl methacrylate formation activity per catalyst unit weight was 2.659 mol/h/kg-cat. Reactivity after 500 hours had elapsed demonstrated decreases in reaction activity and selectivity, yielding a methacrolein conversion rate of 17.8%, methyl methacrylate selectivity of 78.3% and methyl methacrylate formation activity of 1.819 mol/h/kg-cat.

In addition, when the concentrations of Au and Si ions in the reaction solution were analyzed by ICP-MS at 200 and 500 hours after the start of the reaction, the concentrations of Au were 0.1 ppm or less at both times and the concentrations of Si were 1 ppm or less at both times. When the catalyst was extracted after reacting for 500 hours and investigated with a scanning electron microscope (SEM), there was hardly any cracking or chipping of the catalyst particles observed. In addition, catalyst pore volume as determined according to the nitrogen adsorption method was 0.41 mL/g and average pore diameter was 13 nm. The number average particle diameter of the gold nanoparticles as determined with a transmission electron microscope (TEM) was 5.3 nm, and increased catalyst pore diameter and gold nanoparticle sintering were observed.

Comparative Example 11

A catalyst loaded with 1.48% by mass of gold (Au/SiO$_2$—Al$_2$O$_3$—MgO) was obtained by producing a catalyst in the same manner as (2) of Example 25 with the exception of using the silica-alumina-magnesia support prepared in (1) of Example 25 for the support and not adding nickel nitrate hexahydrate. Based on the results of powder X-ray diffraction (XRD) of this catalyst, a broad peak was present corresponding to gold crystals. The average crystallite size as calculated according to Scherrer's formula was about 3 nm. When the form of the gold particles was observed with a transmission electron microscope (TEM), gold particles having an average particle diameter of 3.4 nm were confirmed to be loaded onto the support. In addition, the specific surface area of the catalyst was 152 m²/g, the pore volume of the catalyst as determined by the nitrogen adsorption method was 0.25 mL/g, and the average pore diameter was 5 nm. Moreover, as a result of investigating changes in the electron excitation state of this catalyst by ultraviolet-visible spectroscopy (UV-Vis), a surface plasmon absorption peak originating from gold nanoparticles was observed (at about 530 nm).

A reaction was carried out in the same manner as (3) of Example 17 using this catalyst. As a result, the methacrolein conversion rate after reacting for 200 hours was 29.3%, methyl methacrylate selectivity was 82.3%, and methyl methacrylate formation activity per catalyst unit weight was 3.148 mol/h/kg-cat. Reactivity after 500 hours had elapsed demonstrated decreases in reaction activity and selectivity, yielding a methacrolein conversion rate of 23.5%, methyl methacrylate selectivity of 80.1% and methyl methacrylate formation activity of 2.457 mol/h/kg-cat.

In addition, when the concentrations of Au and Si ions in the reaction solution were analyzed by ICP-MS at 200 and 500 hours after the start of the reaction, the concentrations of Au were 0.1 ppm or less at both times and the concentrations of Si were 1 ppm or less at both times. When the catalyst was extracted after reacting for 500 hours and investigated with a scanning electron microscope (SEM), there was hardly any cracking or chipping of the catalyst particles observed. In addition, catalyst pore volume as determined according to the nitrogen adsorption method was 0.37 mL/g and average pore diameter was 10 nm. The number average particle diameter of the gold nanoparticles as determined with a transmission electron microscope (TEM) was 5.4 nm, and increased catalyst pore diameter and gold nanoparticle sintering were observed.

On the basis of the results described above, the catalyst for use in production of carboxylic acid ester according to the present embodiment efficiently yields carboxylic acid esters at high selectivity from an aldehyde and alcohol or one or more types of alcohols, and demonstrates superior mechanical strength and chemical stability of the support without the occurrence of cracking or chipping of the catalyst even after a long period of time has elapsed. In addition, there is hardly any occurrence of exfoliation or elution of nickel and component X which are catalyst active components, increased catalyst pore diameter or sintering of composite nanoparticles, thereby enabling the catalyst to maintain a high level of reactivity even after a long period of time has elapsed.

The present application is based on a Japanese patent application filed with the Japanese Patent Office on Aug. 13, 2007 (Japanese Patent Application No. 2007-210962), a Japanese patent application filed with the Japanese Patent Office on Oct. 11, 2007 (Japanese Patent Application No. 2007-265375), a Japanese patent application filed with the Japanese Patent Office on Oct. 26, 2007 (Japanese Patent Application No. 2007-279411), and a Japanese patent application filed with the Japanese Patent Office on Apr. 14, 2008 (Japanese Patent Application No. 2008-105103), the contents of which are incorporated herein by reference.

INDUSTRIAL APPLICABILITY

The present invention has the potential for industrial use as a catalyst used when producing carboxylic acid ester by reacting an aldehyde and alcohol, or one or more types of alcohols, in the presence of oxygen.

We claim:

1. A catalyst for use in production of carboxylic acid ester by reacting (a) aldehyde and alcohol, or (b) one or more types of alcohols, in the presence of oxygen, comprising:
   oxidized nickel; and
   X (wherein X represents at least one element selected from the group consisting of palladium, platinum, ruthenium, gold, and silver) loaded onto a support within a range of an atomic ratio of Ni/(Ni+X) of from 0.20 to 0.99.

2. The catalyst for use in production of the carboxylic acid ester according to claim 1, comprising a composite nanoparticle composed of the oxidized nickel and the X (wherein X represents at least one element selected from the group consisting of palladium, platinum, ruthenium, gold, and silver).

3. The catalyst for use in production of the carboxylic acid ester according to claim 2, wherein the composite nanoparticle is a particle having X at a core thereof and a surface of the core is covered with the oxidized nickel.

4. The catalyst for use in production of the carboxylic acid ester according to claim 2 or 3, wherein the oxidized nickel is further independently loaded onto the support, in addition to the composite nanoparticle.

5. The catalyst for use in production of the carboxylic acid ester according to claim 1 or 2, wherein the oxidized nickel is a nickel oxide and/or a composite oxide containing nickel.

6. The catalyst for use in production of the carboxylic acid ester according to claim 1 or 2, wherein the support is an aluminum-containing silica-based composition containing silica and alumina, and an amount of aluminum is within a range of from 1 to 30 mol %, based on a total molar amount of the silicon and the aluminum.

7. The catalyst for use in production of the carboxylic acid ester according to claim 6, wherein the support further comprises at least one species of basic metal component selected from the group consisting of an alkali metal, an alkaline earth metal and a rare earth metal.

8. The catalyst for use in production of the carboxylic acid ester according to claim 7, wherein a compositional ratio of nickel to the basic metal component is from 0.01 to 1.2 in terms of an atomic ratio of Ni/(the alkali metal+the alkaline earth metal+the rare earth metal).

9. The catalyst for use in production of the carboxylic acid ester according to claim 6, wherein a compositional ratio of nickel to alumina is from 0.01 to 1.0 in terms of an atomic ratio of Ni/Al.

10. The catalyst for use in production of carboxylic acid ester according to claim 2, wherein the average particle diameter of X is in the range of 2 to 15 nm.

11. The catalyst for use in production of the carboxylic acid ester according to claim 1 or 2, wherein the support is a silica-alumina-magnesia composition containing silica, alumina and magnesia, and comprises silicon at 42 to 90 mol %, aluminum at 5.5 to 38 mol % and magnesium at 4 to 38 mol %, based on a total molar amount of silicon, aluminum and magnesium.

12. The catalyst for use in production of the carboxylic acid ester according to claim 11, wherein the composition ratio of nickel to alumina is from 0.01 to 1.0 in terms of the atomic ratio of Ni/Al, and the composition ratio of nickel to magnesia is from 0.01 to 1.2 in terms of an atomic ratio of Ni/Mg.

13. The catalyst for use in production of the carboxylic acid ester according to claim 1 or 2, has a specific surface area of from 20 to 350 m²/g, a maximum frequency of a pore diameter is from 3 to 50 nm, a pore volume is from 0.1 to 1.0 mL/g, and a particle diameter is from 10 to 200 μm.

14. A process of producing a catalyst for use in production of carboxylic acid ester according to claim 1, comprising:

a first step of obtaining a catalyst precursor by precipitating nickel and a component X (wherein X represents at least one element selected from the group consisting of palladium, platinum, ruthenium, gold, and silver) on a support by neutralizing an acidic solution of a soluble metal salt containing nickel and X; and a second step of oxidizing the nickel by heat-treating the obtained catalyst precursor.

15. A process for producing carboxylic acid ester comprising a step of reacting the catalyst for use in production of carboxylic acid ester according to claim 1 or 2, with (a) aldehyde and alcohol, or (b) one or more types of alcohols, in the presence of oxygen.

16. The process for producing carboxylic acid ester according to claim 15, wherein the aldehyde is a compound selected from acrolein, methacrolein and a mixture thereof.

17. The process for producing carboxylic acid ester according to claim 15, wherein the aldehyde is a compound selected from acrolein, methacrolein and a mixture thereof, and the alcohol is methanol.

18. The process for producing carboxylic acid ester according to claim 15, wherein one type of the alcohol is ethylene glycol, and another type of the alcohol is methanol.

\* \* \* \* \*

UNITED STATES PATENT AND TRADEMARK OFFICE
CERTIFICATE OF CORRECTION

| | | |
|---|---|---|
| PATENT NO. | : 8,461,373 B2 | Page 1 of 1 |
| APPLICATION NO. | : 12/673159 | |
| DATED | : June 11, 2013 | |
| INVENTOR(S) | : Suzuki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 213 days.

Signed and Sealed this
Thirtieth Day of December, 2014

Michelle K. Lee
*Deputy Director of the United States Patent and Trademark Office*